US007563595B2

(12) United States Patent
Cuevas et al.

(10) Patent No.: US 7,563,595 B2
(45) Date of Patent: Jul. 21, 2009

(54) NUCLEIC ACIDS ENCODING FUNCTIONAL SPLICE VARIANTS OF THE α7 NICOTINIC ACETYLCHOLINE RECEPTOR SUBUNIT AND METHODS FOR PRODUCING THE ENCODED PROTEINS

(75) Inventors: Javier Cuevas, Lutz, FL (US); Emily Severance, Lutz, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 10/703,953

(22) Filed: Nov. 7, 2003

(65) Prior Publication Data

US 2004/0152160 A1 Aug. 5, 2004

Related U.S. Application Data

(60) Provisional application No. 60/320,085, filed on Apr. 4, 2003, provisional application No. 60/319,678, filed on Nov. 8, 2002.

(51) Int. Cl.
*C12P 21/02* (2006.01)
*C12N 1/21* (2006.01)
*C12N 15/12* (2006.01)
*C07H 21/04* (2006.01)

(52) U.S. Cl. ............... 435/69.1; 435/320.1; 435/252.3; 435/254.2; 435/325; 536/23.5

(58) Field of Classification Search .................. None
See application file for complete search history.

(56) References Cited

U.S. PATENT DOCUMENTS

| 5,683,912 | A | * | 11/1997 | Elgoyhen et al. | .......... | 435/252.3 |
|---|---|---|---|---|---|---|
| 5,866,114 | A | * | 2/1999 | Pandit et al. | .............. | 424/85.1 |
| 6,194,183 | B1 | * | 2/2001 | Markvardsen et al. | ...... | 435/183 |
| 2003/0165843 | A1 | * | 9/2003 | Shoshan et al. | ................ | 435/6 |

OTHER PUBLICATIONS

Simosky 2001. Biological Psychiatry 50:493-500.*
Meyer et al. 1998. Journal of Pharmacology and Experimental Therapeutics 284:1026-1032.*
Buhr et al. 1997. Proc Natl. Acad Sci USA 94:8824-8829.*
Galzi et al. 1992. Nature 359:500-505.*
Strauss 1993. Current Protocols in Molecular Biology 6.3.1-6.3.6.*
Severance 2002. 32nd Annual Meeting of the Society for Neuroscience, Nov. 2-7, 2002, abstract 617.3.*
Schendel 1998. Current Protocols in Molecular Biology 16.1.1-16.1.3.*
Peng 1994. Molecular Pharmacology 45:546-554.*
Severance 2001. Society for Neuroscience Abstracts 27(1):375.*
Placzek et al. 2001. Society for Neuroscience Abstracts 27(1):375.*
Gault 1998. Genomics 52:173-185.*
Alberts et al., Molecular Biology of the Cell, 3rd Edition, 1994, pp. 98-104.*
Benowitz, N.L. "Pharmacology of nicotine: Addiction and therapeutics" *Annu. Rev. Pharmacol. Toxicol.*, 1996, 36:597-613.

Bertrand, D. et al. "Unconventional pharmacology of a neuronal nicotinic receptor mutated in the channel domain" *Proc. Natl. Acad. Sci. USA*, 1992, 89:1261-1265.
Buisson, B. et al. "Human α4β2 neuronal nicotinic acetylcholine receptor in HEK 293 cells: A patch-damp study" *J. Neurosci.*, 1996, 16(24):7880-7891.
Cooper, E.C. and Jan, L.Y. "Ion channel genes and human neurological disease: Recent progress, prospects, and challenges" *Proc. Natl. Acad. Sci. USA*, 1999, 96:4759-4766.
Cuevas, J. et al. "Two distinct classes of functional α7-containing nicotinic receptor on rat superior cervical ganglion neurons" *J. Physiology*, 2000, 525.3, pp. 735-746.
Cuevas, J. and Berg, D.K. "Mammalian nicotinic receptors with α7 subunits that slowly desensitize and rapidly recover from α-bungarotoxin blockade" *J. Neurosci.*, 1998, 18(24):10335-10344.
Francis, M.M. et al. "Specific activation of the α7 nicotinic acetylcholine receptor by a quaternary analog of cocaine" *Mol. Pharmacol.*, 2001, 60(1):71-79.
Freedman, R. et al. "The α7-nicotinic acetylcholine receptor and the pathology of hippocampal interneurons in schizophrenia" *J. Chem. Neuroanatomy*, 2000, 20:299-306.
Freedman, R. et al. "Schizophrenia and nicotinic receptors" *Harvard Rev. Psychiatry*, 1994, 2:179-192.
Holladay, M.W. et al. "Neuronal nicotinic acetylcholine receptors as targets for drug discovery" *J. Med. Chem.*, 1997, 40(26):4169-4194.
Jonnala, R.R. and Buccafusco, J.J. "Relationship between the increased cell surface α7 nicotinic receptor expression and neuroprotection induced by several nicotinic receptor agonists" *J. Neurosci. Res.*, 2001, 66:565-572.
Kehoe, J. and McIntosh, J.M. "Two distinct nicotinic receptors, one pharmacologically similar to the vertebrate α7-containing receptor, mediate Cl currents in *Aplysia* neurons" *J. Neurosci.*, 1998, 18(2):8198-8213.
Lloyd, G.K. and Williams, M. "Neuronal nicotinic acetylcholine receptors as novel drug targets" *J. Pharmacol. Exp. Therapeutics*, 2000, 292(2):461-467.
Meyer, E.M. et al. "Neuroprotective and memory-related actions of novel *Alpha*-7 nicotinic agents with different mixed agonist-antagonist properties" *J. Pharmacol. Exp. Therapeutics*, 1998, 284(3):1026-1032.
Mihailescu, S. and Drucker-Colin, R. "Nicotine, brain nicotinic receptors, and neuropsychiatric disorders" *Arch. Med. Res.*, 2000, 31:131-144.
Newhouse, P.A. and Kelton, M. "Nicotinic systems in central nervous systems disease: degenerative disorders and beyond" *Pharmaceutica Acta Helvetiae*, 2000, 74:91-101.

(Continued)

*Primary Examiner*—Daniel E. Kolker
(74) *Attorney, Agent, or Firm*—Saliwanchik, Lloyd & Saliwanchik

(57) ABSTRACT

The present invention concerns a novel α7 nicotinic receptor subunit isoform, α7-2. The α7-2 isoform contributes to novel acetylcholine receptors (AChRs) with pharmacological and biophysical properties distinct from those of wild-type α7-1-nAChRs and closely resembling those of α7-nAChRs found in intrinsic cardiac neurons and Type II α7-nAChRs of superior cervical ganglion neurons. Polynucleotides encoding the α7-2 isoform, vectors and genetically modified cells containing such polynucleotides are also provided. In addition, methods are provided for producing the α7-2 isoform as are methods of using such isoforms for screening compounds for activity at the nAChR.

9 Claims, 7 Drawing Sheets

OTHER PUBLICATIONS

Newhouse, P.A. et al. "Nicotinic system involvement in Alzheimer's and Parkinson's diseases" *Drugs & Aging*, 1997, 11(3):206-228.

Papke, R.L. et al. "α7 receptor-selective agonists and modes of α7 receptor activation" *Euro. J. Pharmacol.*, 2000, 393:179-195.

Salamone, F. and Zhou, M. "Aberrations in nicotinic acetylcholine receptor structure, function, and expression: Implications in disease" *McGill J. Med.*, 2000, 5:90-97.

Sharples, C. and Wonnacott, S. "Neuronal nicotinic receptors" *Tocris Reviews*, Oct. 2001, No. 19, pp. 1-12.

Bruss, M. et al. "Modified 5-HT3A receptor function by co-expression of alternatively spliced human 5-HT3A receptor isoforms" *Naunyn-Schmiedeberg's Archives of Pharmacology*, 2000, 362:392-401.

Connolly, J. et al. "Alpha 4-2 beta 2 and other nicotinic acetylcholine receptor subtypes as targets of psychoactive and addictive drugs" *Brit. J. Pharmacol.*, 1992, 105:657-686.

Cuevas, J. and Berg, D.K. "Mammalian nicotinic receptors with α7 subunits that slowly desensitize and rapidly recover from α-bungarotoxin blockade" *J.Neurosci.*, 1998, 18:10335-10344.

Garcia-Guzman, M. et al. "α-Bungarotoxin-sensitive nicotinic receptors on bovine chromaffin cells: molecular cloning, functional expression and alternative splicing of the α7 subunit" *Eur. J. Neurosci.*, 1995, 7:647-655.

Gault, J. et al. "Genomic organization and partial duplication of the human α7 neuronal nicotinic acetylcholine receptor gene (CHRNA7)" *Genomics*, 1998, 52:173-185.

Newland, C.F. et al. "Functional and non-functional isoforms of the human muscle acetylcholine receptor" *J. Physiol.*, 1995, 489:767-778.

Quinlan, J.J. et al. "Mice lacking the long splices variant of the γ2 subunit of the GABA(A) receptor are more sensitive to benzodiazepines" *Pharmacol Biochem Behav.*, 2000, 66:371-374.

Saragoza, P.A. et al. "Identification of an alternatively processed nicotinic receptor alpha7 subunit RNA in mouse brain" *Brain Research. Molecular Brain Research*, 2003, 117:15-26.

Severance, E.G. and Cuevas, J. "Identification of a novel exon in the mammalian alpha7 nicotinic acetylcholine receptor subunit gene" poster presentation presented at the 31st Annual Meeting for the Society for Neuroscience, Nov. 10-15, 2001.

Severance, E.G. et al. "Tissue distribution and functional expression of the mammalian α7-2 nicotinic acetylcholine receptor subunit isoform" poster presentation presented at the 32nd Annual Meeting of the Society for Neuroscience, Nov. 2-7, 2002.

* cited by examiner

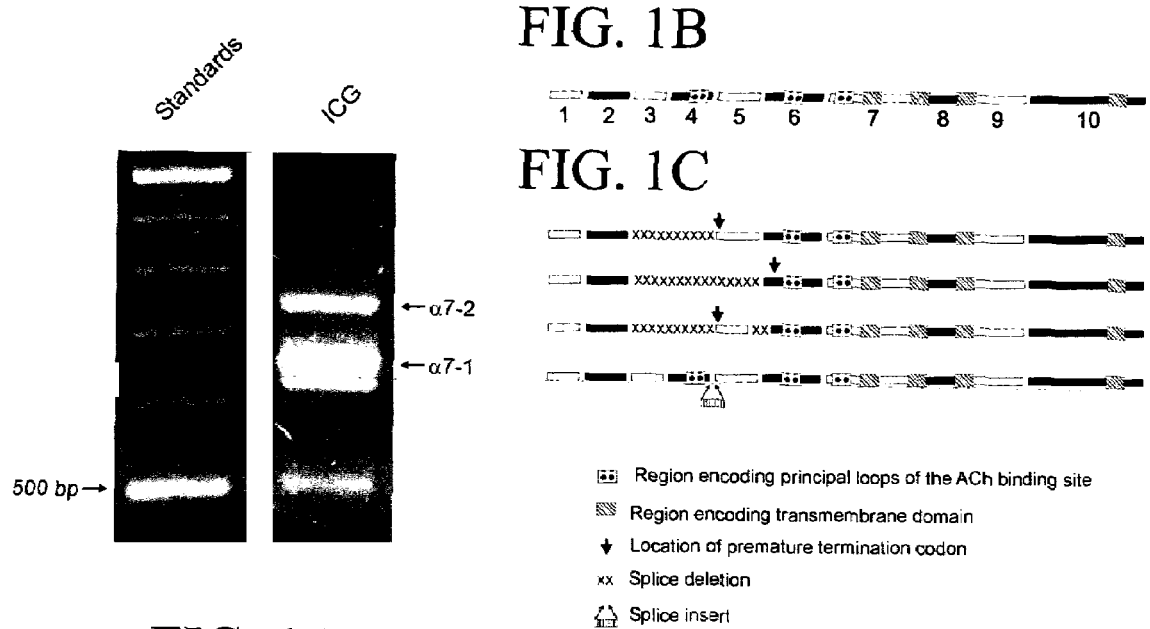
FIG. 1A
FIG. 1B
FIG. 1C
- Region encoding principal loops of the ACh binding site
- Region encoding transmembrane domain
- ↓ Location of premature termination codon
- xx Splice deletion
- Splice insert
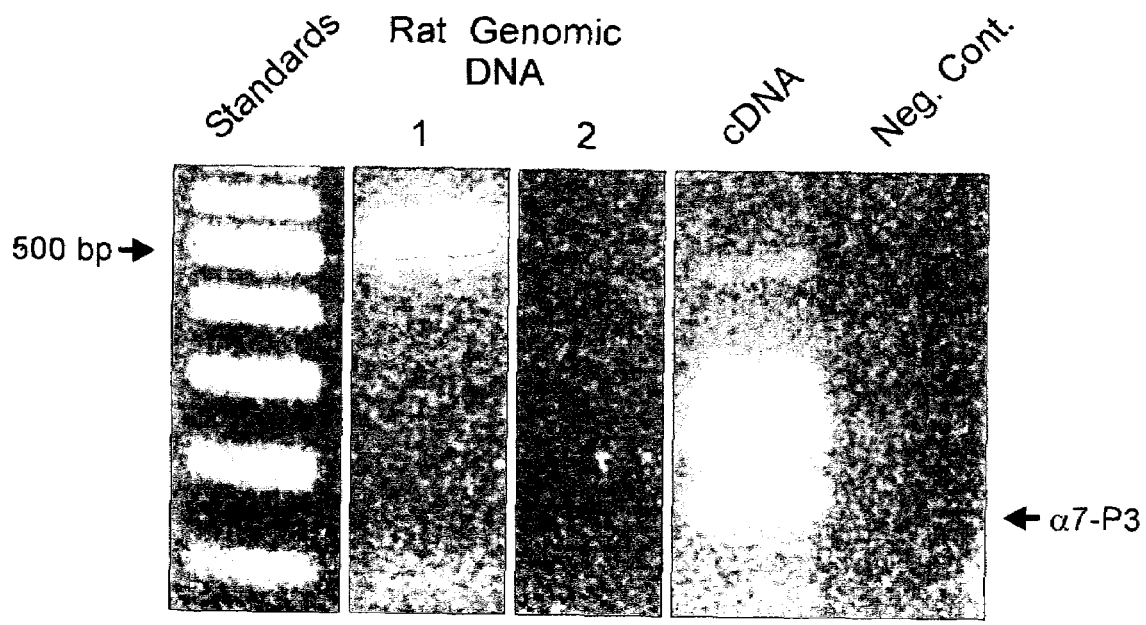
FIG. 3

```
RATNARAD  109 GTACAAGGAGCTGGTCAAGAACTACAACCCGCTGGAGAGGCCGGTGGCCAACGACTCGCA
α7-2        1 GTACAAGGAGCTGGTCAAGAACTACAACCCGCTGGAGAGGCCGGTGGCCAACGACTCGCA
               Y  K  E  L  V  K  N  Y  N  P  L  E  R  P  V  A  N  D  S  Q

RATNARAD  169 GCCGCTCACCGTGTACTTCTCCCTGAGTCTCCTGCAGATCATGGATGTGGATGAGAAGAA
α7-2       61 GCCGCTCACCGTGTACTTCTCCCTGAGTCTCCTGCAGATCATGGATGTGGATGAGAAGAA
               P  L  T  V  Y  F  S  L  S  L  L  Q  I  M  D  V  D  E  K  N

RATNARAD  229 CCAAGTTTTAACCACCAACATTTGGCTACAAATGTCTTGGACAGATCACTATTTGCAGTG
α7-2      121 CCAAGTTTTAACCACCAACATTTGGCTACAAATGTCTTGGACAGATCACTATTTGCAGTG
               Q  V  L  T  T  N  I  W  L  Q  M  S  W  T  D  H  Y  L  Q  W

RATNARAD  289 GAACATGTCTGAGTACCCCGGAGTGAAGAATGTTCGTTTTCCAGATGGCCAGATTTGGAA
α7-2      181 GAACATGTCTGAGTACCCCGGAGTGAAGAATGTTCGTTTTCCAGATGGCCAGATTTGGAA
               N  M  S  E  Y  P  G  V  K  N  V  R  F  P  D  G  Q  I  W  K

RATNARAD  349 ACCAGACATTCTCCTCTATAACAGT------------------------------------
α7-2      241 ACCAGACATTCTCCTCTATAACAGTGGGTGTCAGTTGCATTTTGACCAAGATCTGCAGAA
               P  D  I  L  L  Y  N  S  G  C  Q  L  H  F  D  Q  D  L  Q  N

RATNARAD  375 ----------------------------------------------------GCTGATGA
α7-2      301 CATGCTTCTCAGAGAAGCATGTGCACAGGCTGGAGAAGATCTAAGAGTCAGTGCTGATGA
               M  L  L  R  E  A  C  A  Q  A  G  E  D  L  R  V  S  A  D  E

RATNARAD  382 GCGCTTTGATGCCACGTTCCACACCAATGTTTTGGTGAATGCATCTGGGCATTGCCAGTA
α7-2      361 GCGCTTTGATGCCACGTTCCACACCAATGTTTTGGTGAATGCATCTGGGCATTGCCAGTA
               R  F  D  A  T  F  H  T  N  V  L  V  N  A  S  G  H  C  Q  Y

RATNARAD  442 TCTCCCTCCAGGCATATTCAAGAGCTCCTGCTACATTGACGTTCGCTGGTTCCCTTTTGA
α7-2      421 TCTCCCTCCAGGCATATTCAAGAGCTCCTGCTACATTGACGTTCGCTGGTTCCCTTTTGA
               L  P  P  G  I  F  K  S  S  C  Y  I  D  V  R  W  F  P  F  D

RATNARAD  502 TGTGCAGCAGTGCAAACTGAAGTTTGGGTCCTGGTCCTATGGAGGGTGGTCACTGGACCT
α7-2      481 TGTGCAGCAGTGCAAACTGAAGTTTGGGTCCTGGTCCTATGGAGGGTGGTCACTGGACCT
               V  Q  Q  C  K  L  K  F  G  S  W  S  Y  G  G  W  S  L  D  L

RATNARAD  562 GCAAATGCAAGAGGCAGATATCAGCAGCTATATCCCCAACGGAGAATGGGATCTCATGGG
α7-2      541 GCAAATGCAAGAGGCAGATATCAGCAGCTATATCCCCAACGGAGAATGGGATCTCATGGG
               Q  M  Q  E  A  D  I  S  S  Y  I  P  N  G  E  W  D  L  M  G

RATNARAD  622 AATCCCTGGCAAAAGGAATGAGAAGTTCTATGAGTGCTGCAAAGAGCCATACCCAGATGT
α7-2      601 AATCCCTGGCAAAAGGAATGAGAAGTTCTATGAGTGCTGCAAAGAGCCATACCCAGATGT
               I  P  G  K  R  N  E  K  F  Y  E  C  C  K  E  P  Y  P  D  V

RATNARAD  682 CACCTACACAGTAACCATGCGCCGTAGGACACTCTACTATGGCCTCAATCTGCTCATCCC
α7-2      661 CACCTACACAGTAACCATGCGCCGTAGGACACTCTACTATGGCCTCAATCTGCTCATCCC
               T  Y  T  V  T  M  R  R  R  T  L  Y  Y  G  L  N  L  L  I  P

RATNARAD  742 TTGTGTACTCATTTCAGCCC
α7-2      721 TTGTGTACTCATTTCAGCCC
               C  V  L  I  S  A
```

FIG. 2

```
α7-2     1  GGAGTGAAGAATGTTCGTTTTCCAGATGGCCAGATTTGGAAACCAGACATTCTCCTCTAT
α7-gene  1  GGAGTGAAGAATGTTCGTTTTCCAGATGGCCAGATTTGGAAACCAGACATTCTCCTCTAT α7-2     61 AACAG-------------------------------------------------------
α7-gene  61 AACAGgtaagcacgcctgacagatgggaaacaatcttcacttgcatgcatggggcgataa α7-2     66 ------------------------------------------------------------
α7-gene  121 agcatatttgaggattttacagaaaagctggctgtgttatctttaatttggaaccattgc α7-2     66 ------------------------------------------------------------
α7-gene  181 tccttttgaggctttccaagtgggcagatctctgggaggctgctctgtccctctgctggt α7-2     66 ------------------------------------------------------------
α7-gene  241 atttgtgtctaagtttaggttgtctctccttctgccagaaatgtcctgtccaagggggctg α7-2     66 ------------------------------------------------------------
α7-gene  301 aactatagatacataaaggtgttcaccatttatagcaatgtaaagcattcttaaggcagt α7-2     66 ------------------------------------------------------------
α7-gene  361 cactttgctatctgaatggcaaccattacaacccacagaagaaggtgccagacagcatgt α7-2     66 ---------------------------------------------------------TG
α7-gene  421 gcattggagactacagttaagacctaggttctcatctgacttttttccccattgttcagTG α7-2     68 GGTGTCAGTTGCATTTTGACCAAG
α7-gene  481 GGTGTCAGTTGCATTTTGACCAAG
```

FIG. 4

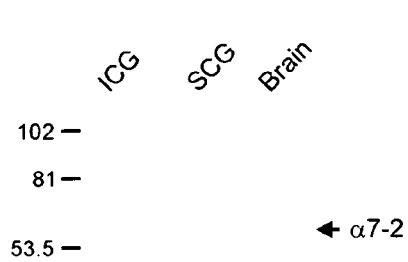
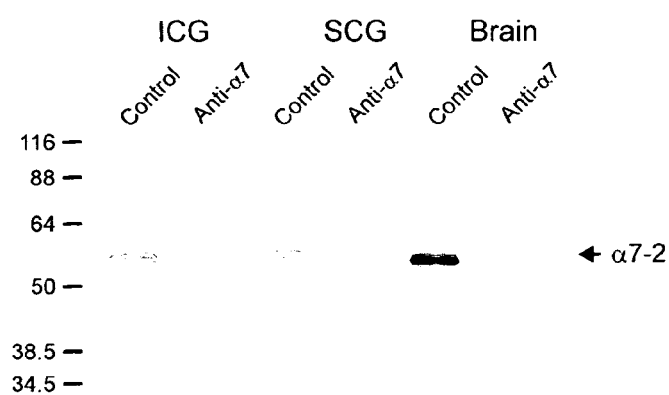
FIG. 6A                    FIG. 6B

SEQUENCE LISTING

```
<160> NUMBER OF SEQ ID NOS: 16

<210> SEQ ID NO 1
<211> LENGTH: 531
<212> TYPE: PRT
<213> ORGANISM: Rattus norvegicus
<220> FEATURE:
<221> NAME/KEY: MISC_FEATURE
<222> LOCATION: (1)..(531)
<223> OTHER INFORMATION: amino acid sequence of alpha-7-2 subunit splice
      variant

<400> SEQUENCE: 1

Met Cys Gly Gly Arg Gly Gly Ile Trp Leu Ala Leu Ala Ala Ala Leu
1               5                   10                  15

Leu His Val Ser Leu Gln Gly Glu Phe Gln Arg Arg Leu Tyr Lys Glu
            20                  25                  30

Leu Val Lys Asn Tyr Asn Pro Leu Glu Arg Pro Val Ala Asn Asp Ser
```

-continued

```
              35                  40                  45
Gln Pro Leu Thr Val Tyr Phe Ser Leu Ser Leu Leu Gln Ile Met Asp
 50                  55                  60
Val Asp Glu Lys Asn Gln Val Leu Thr Thr Asn Ile Trp Leu Gln Met
 65                  70                  75                  80
Ser Trp Thr Asp His Tyr Leu Gln Trp Asn Met Ser Glu Tyr Pro Gly
                 85                  90                  95
Val Lys Asn Val Arg Phe Pro Asp Gly Gln Ile Trp Lys Pro Asp Ile
                100                 105                 110
Leu Leu Tyr Asn Ser Gly Cys Gln Leu His Phe Asp Gln Asp Leu Gln
                115                 120                 125
Asn Met Leu Leu Arg Glu Ala Cys Ala Gln Ala Gly Glu Asp Leu Arg
130                 135                 140
Val Ser Ala Asp Glu Arg Phe Asp Ala Thr Phe His Thr Asn Val Leu
145                 150                 155                 160
Val Asn Ala Ser Gly His Cys Gln Tyr Leu Pro Pro Gly Ile Phe Lys
                165                 170                 175
Ser Ser Cys Tyr Ile Asp Val Arg Trp Phe Pro Phe Asp Val Gln Gln
                180                 185                 190
Cys Lys Leu Lys Phe Gly Ser Trp Ser Tyr Gly Gly Trp Ser Leu Asp
                195                 200                 205
Leu Gln Met Gln Glu Ala Asp Ile Ser Ser Tyr Ile Pro Asn Gly Glu
                210                 215                 220
Trp Asp Leu Met Gly Ile Pro Gly Lys Arg Asn Glu Lys Phe Tyr Glu
225                 230                 235                 240
Cys Cys Lys Glu Pro Tyr Pro Asp Val Thr Tyr Thr Val Thr Met Arg
                245                 250                 255
Arg Arg Thr Leu Tyr Tyr Gly Leu Asn Leu Leu Ile Pro Cys Val Leu
                260                 265                 270
Ile Ser Ala Leu Ala Leu Leu Val Phe Leu Leu Pro Ala Asp Ser Gly
                275                 280                 285
Glu Lys Ile Ser Leu Gly Ile Thr Val Leu Leu Ser Leu Thr Val Phe
                290                 295                 300
Met Leu Leu Val Ala Glu Ile Met Pro Ala Thr Ser Asp Ser Val Pro
305                 310                 315                 320
Leu Ile Ala Gln Tyr Phe Ala Ser Thr Met Ile Ile Val Gly Leu Ser
                325                 330                 335
Val Val Val Thr Val Ile Val Leu Arg Tyr His His His Asp Pro Asp
                340                 345                 350
Gly Gly Lys Met Pro Lys Trp Thr Arg Ile Ile Leu Leu Asn Trp Cys
                355                 360                 365
Ala Trp Phe Leu Arg Met Lys Arg Pro Gly Glu Asp Lys Val Arg Pro
                370                 375                 380
Ala Cys Gln His Lys Pro Arg Arg Cys Ser Leu Ala Ser Val Glu Leu
385                 390                 395                 400
Ser Ala Gly Ala Gly Pro Pro Thr Ser Asn Gly Asn Leu Leu Tyr Ile
                405                 410                 415
Gly Phe Arg Gly Leu Glu Gly Met His Cys Ala Pro Thr Pro Asp Ser
                420                 425                 430
Gly Val Val Cys Gly Arg Leu Ala Cys Ser Pro Thr His Asp Glu His
                435                 440                 445
Leu Met His Gly Ala His Pro Ser Asp Gly Asp Pro Asp Leu Ala Lys
                450                 455                 460
```

```
Ile Leu Glu Glu Val Arg Tyr Ile Ala Asn Arg Phe Arg Cys Gln Asp
465                 470                 475                 480

Glu Ser Glu Val Ile Cys Ser Glu Trp Lys Phe Ala Ala Cys Val Val
                485                 490                 495

Asp Arg Leu Cys Leu Met Ala Phe Ser Val Phe Thr Ile Ile Cys Thr
            500                 505                 510

Ile Gly Ile Leu Met Ser Ala Pro Asn Phe Val Glu Ala Val Ser Lys
        515                 520                 525

Asp Phe Ala
    530

<210> SEQ ID NO 2
<211> LENGTH: 1605
<212> TYPE: DNA
<213> ORGANISM: Rattus norvegicus
<220> FEATURE:
<221> NAME/KEY: misc_feature
<222> LOCATION: (1)..(1605)
<223> OTHER INFORMATION: nucleotide sequence encoding alpha7-2 subunit
      splice variant

<400> SEQUENCE: 2
atgtgcggcg ggcggggagg catctggctg gctctggccg cggcgctgct gcacgtgtcc     60
ctgcaaggcg agttccagag gaggctgtac aaggagctgg tcaagaacta caacccgctg    120
gagaggccgg tggccaacga ctcgcagccg ctcaccgtgt acttctccct gagtctcctg    180
cagatcatgg atgtggatga aaagaaccaa gttttaacca ccaacatttg gctacaaatg    240
tcttggacag atcactattt gcagtggaac atgtctgagt accccggagt gaagaatgtt    300
cgttttccag atgccagat ttggaaacca gacattctcc tctataacag tgggtgtcag    360
ttgcattttg accaagatct gcagaacatg cttctcagag aagcatgtgc acaggctgga    420
gaagatctaa gagtcagtgc tgatgagcgc tttgatgcca cgttccacac caatgttttg    480
gtgaatgcat ctgggcattg ccagtatctc cctccaggca tattcaagag ctcctgctac    540
attgacgttc gctggttccc ttttgatgtg cagcagtgca aactgaagtt tgggtcctgg    600
tcctatggag ggtggtcact ggacctgcaa atgcaagagg cagatatcag cagctatatc    660
cccaacggag aatgggatct catgggaatc cctggcaaaa ggaatgagaa gttctatgag    720
tgctgcaaag agccataccc agatgtcacc tacacagtaa ccatgcgccg taggacactc    780
tactatggcc tcaatctgct catcccttgt gtactcattt cagccctggc tctgctggta    840
ttcttgctgc ctgcagactc tggagagaaa atctctcttg gataactgt cttactttct    900
ctgactgtct tcatgctgct gtggctgag atcatgccag caacatctga ttctgtgccc    960
ttgatagcac aatacttcgc cagcaccatg atcatcgtgg gcctctctgt agtggtgaca   1020
gtgattgtgc tgagatatca ccaccatgac cctgatggtg gcaaaatgcc taagtggacc   1080
agaatcattc tcctgaactg tgtgcatgg tttctgcgca tgaagaggcc cggagaggac   1140
aaggtgcggc cagcttgtca gcacaagcct cggcgctgca gcctggccag tgtggagctg   1200
agtgcaggtg ctgggccacc caccagcaat ggcaacctgc tctacattgg cttccgaggc   1260
ctggagggca tgcactgtgc cccaactcca gactctgggg tcgtatgtgg ccgtttggcc   1320
tgctccccaa cacatgatga gcacctcatg cacggtgcac acccctctga tggggacccc   1380
gacctggcca agatcctgga ggaggtccgc tacatcgcca accgcttccg ctgccaggac   1440
gagagtgagg tgatctgcag tgaatggaag tttgcagcct gcgtggtgga ccgcttgtgc   1500
```

```
ctcatggcct tttcggtctt taccatcatc tgtaccatcg gcatcctcat gtcagctcca    1560
aactttgtgg aggctgtgtc caaagacttt gcttaatgtt atcaa                    1605

<210> SEQ ID NO 3
<211> LENGTH: 653
<212> TYPE: DNA
<213> ORGANISM: Rattus norvegicus
<220> FEATURE:
<221> NAME/KEY: misc_feature
<222> LOCATION: (1)..(653)
<223> OTHER INFORMATION: nucleotide sequence encoding wild-type alpha7
      subunit (alpha7-1)

<400> SEQUENCE: 3
gtacaaggag ctggtcaaga actacaaccc gctggagagg ccggtggcca acgactcgca      60
gccgctcacc gtgtacttct ccctgagtct cctgcagatc atggatgtgg atgagaagaa     120
ccaagtttta accaccaaca tttggctaca aatgtcttgg acagatcact atttgcagtg     180
gaacatgtct gagtaccccg gagtgaagaa tgttcgtttt ccagatggcc agatttggaa     240
accagacatt ctcctctata cagtgctga tgagcgcttt gatgccacgt tccacaccaa      300
tgttttggtg aatgcatctg gcattgcca gtatctccct ccaggcatat tcaagagctc     360
ctgctacatt gacgttcgct ggttcccttt tgatgtgcag cagtgcaaac tgaagtttgg     420
gtcctggtcc tatggagggt ggtcactgga cctgcaaatg caagaggcag atatcagcag     480
ctatatcccc aacggagaat gggatctcat gggaatccct ggcaaaagga atgaaagtt     540 ctatgagtgc tgcaaagagc catacccaga tgtcacctac acagtaacca tgcgccgtag     600
gacactctac tatggcctca atctgctcat cccttgtgta ctcatttcag ccc            653

<210> SEQ ID NO 4
<211> LENGTH: 217
<212> TYPE: PRT
<213> ORGANISM: Rattus norvegicus
<220> FEATURE:
<221> NAME/KEY: MISC_FEATURE
<222> LOCATION: (1)..(217)
<223> OTHER INFORMATION: amino acid sequence of the wild-type alpha7
      subunit (alpha7-1)

<400> SEQUENCE: 4

Tyr Lys Glu Leu Val Lys Asn Tyr Asn Pro Leu Glu Arg Pro Val Ala
1               5                   10                  15

Asn Asp Ser Gln Pro Leu Thr Val Tyr Phe Ser Leu Ser Leu Leu Gln
            20                  25                  30

Ile Met Asp Val Asp Glu Lys Asn Gln Val Leu Thr Thr Asn Ile Trp
        35                  40                  45

Leu Gln Met Ser Trp Thr Asp His Tyr Leu Gln Trp Asn Met Ser Glu
    50                  55                  60

Tyr Pro Gly Val Lys Asn Val Arg Phe Pro Asp Gly Gln Ile Trp Lys
65                  70                  75                  80

Pro Asp Ile Leu Leu Tyr Asn Ser Ala Asp Glu Arg Phe Asp Ala Thr
                85                  90                  95

Phe His Thr Asn Val Leu Val Asn Ala Ser Gly His Cys Gln Tyr Leu
            100                 105                 110

Pro Pro Gly Ile Phe Lys Ser Ser Cys Tyr Ile Asp Val Arg Trp Phe
        115                 120                 125

Pro Phe Asp Val Gln Gln Cys Lys Leu Lys Phe Gly Ser Trp Ser Tyr
    130                 135                 140
```

Gly Gly Trp Ser Leu Asp Leu Gln Met Gln Glu Ala Asp Ile Ser Ser
145                 150                 155                 160

Tyr Ile Pro Asn Gly Glu Trp Asp Leu Met Gly Ile Pro Gly Lys Arg
                165                 170                 175

Asn Glu Lys Phe Tyr Glu Cys Cys Lys Glu Pro Tyr Pro Asp Val Thr
            180                 185                 190

Tyr Thr Val Thr Met Arg Arg Arg Thr Leu Tyr Tyr Gly Leu Asn Leu
        195                 200                 205

Leu Ile Pro Cys Val Leu Ile Ser Ala
    210                 215

<210> SEQ ID NO 5
<211> LENGTH: 87
<212> TYPE: DNA
<213> ORGANISM: Rattus norvegicus
<220> FEATURE:
<221> NAME/KEY: misc_feature
<222> LOCATION: (1)..(87)
<223> OTHER INFORMATION: nucleotide sequence of the alpha7-2 variant 4a
      exon

<400> SEQUENCE: 5
gggtgtcagt tgcattttga ccaagatctg cagaacatgc ttctcagaga agcatgtgca    60
caggctggag aagatctaag agtcagt                                       87

<210> SEQ ID NO 6
<211> LENGTH: 29
<212> TYPE: DNA
<213> ORGANISM: Artificial Sequence
<220> FEATURE:
<223> OTHER INFORMATION: forward primer alpha7-P1

<400> SEQUENCE: 6
gtacaaggag ctggtcaaga actacaacc                                     29

<210> SEQ ID NO 7
<211> LENGTH: 22
<212> TYPE: DNA
<213> ORGANISM: Artificial Sequence
<220> FEATURE:
<223> OTHER INFORMATION: reverse primer alpha7-P1

<400> SEQUENCE: 7
gggctgaaat gagtacacaa gg                                            22

<210> SEQ ID NO 8
<211> LENGTH: 25
<212> TYPE: DNA
<213> ORGANISM: Artificial Sequence
<220> FEATURE:
<223> OTHER INFORMATION: forward primer alpha7-P2

<400> SEQUENCE: 8
ggagtgaaga atgttcgttt tccag                                         25

<210> SEQ ID NO 9
<211> LENGTH: 24
<212> TYPE: DNA
<213> ORGANISM: Artificial Sequence
<220> FEATURE:
<223> OTHER INFORMATION: reverse primer alpha7-P2

<400> SEQUENCE: 9
cttggtcaaa atgcaactga cacc                                          24

<210> SEQ ID NO 10
<211> LENGTH: 24
<212> TYPE: DNA
<213> ORGANISM: Artificial Sequence
<220> FEATURE:
<223> OTHER INFORMATION: forward primer alpha7-P3

<400> SEQUENCE: 10
agttgcattt tgaccaagat ctgc                                          24

<210> SEQ ID NO 11
<211> LENGTH: 22
<212> TYPE: DNA
<213> ORGANISM: Artificial Sequence
<220> FEATURE:
<223> OTHER INFORMATION: reverse primer alpha7-P3

<400> SEQUENCE: 11
caaaacattg gtgtggaacg tg                                            22

<210> SEQ ID NO 12
<211> LENGTH: 24
<212> TYPE: DNA
<213> ORGANISM: Artificial Sequence
<220> FEATURE:
<223> OTHER INFORMATION: forward primer alpha7-P4

<400> SEQUENCE: 12
ggtgtcagtt gcattttgac caag                                          24

<210> SEQ ID NO 13
<211> LENGTH: 22
<212> TYPE: DNA
<213> ORGANISM: Artificial Sequence
<220> FEATURE:
<223> OTHER INFORMATION: reverse primer alpha7-P4

<400> SEQUENCE: 13
gggctgaaat gagtacacaa gg                                            22

<210> SEQ ID NO 14
<211> LENGTH: 76
<212> TYPE: DNA
<213> ORGANISM: Mus musculus
<220> FEATURE:
<221> NAME/KEY: misc_feature
<222> LOCATION: (1)..(76)
<223> OTHER INFORMATION: nucleotide sequence of alpha7-2 variant 4a exon

<400> SEQUENCE: 14
gtgtctgttg cattttgacc aagatcggca gaacatgctt ctcagagaaa catatgcaca   60
ggctgaagaa gatcta                                                   76

<210> SEQ ID NO 15
<211> LENGTH: 29
<212> TYPE: PRT
<213> ORGANISM: Rattus norvegicus
<220> FEATURE:
<221> NAME/KEY: MISC_FEATURE
<222> LOCATION: (1)..(29)
<223> OTHER INFORMATION: amino acid sequence of the alpha7-2 variant 4a
      exon

<400> SEQUENCE: 15

Gly Cys Gln Leu His Phe Asp Gln Asp Leu Gln Asn Met Leu Leu Arg

```
                 1               5               10              15
            Glu Ala Cys Ala Gln Ala Gly Glu Asp Leu Arg Val Ser
                        20              25

<210> SEQ ID NO 16
<211> LENGTH: 2106
<212> TYPE: DNA
<213> ORGANISM: Rattus norvegicus
<220> FEATURE:
<221> NAME/KEY: misc_feature
<222> LOCATION: (1)..(2106)
<223> OTHER INFORMATION: nucleotide sequence of alpha7-1 subunit,
      including non-coding regions

<400> SEQUENCE: 16
gccgtgctgc cgctccagcg acatgtgcgg cgggcgggga ggcatctggc tggctctggc        60
cgcggcgctg ctgcacgtgt ccctgcaagg cgagttccag aggaggctgt acaaggagct       120
ggtcaagaac tacaacccgc tggagaggcc ggtggccaac gactcgcagc cgctcaccgt       180
gtacttctcc ctgagtctcc tgcagatcat ggatgtggat gagaagaacc aagttttaac       240
caccaacatt tggctacaaa tgtcttggac agatcactat ttgcagtgga acatgtctga       300
gtaccccgga gtgaagaatg ttcgttttcc agatggccag atttggaaac agacattct       360 cctctataac agtgctgatg agcgctttga tgccacgttc cacaccaatg ttttggtgaa       420
tgcatctggg cattgccagt atctccctcc aggcatattc aagagctcct gctacattga       480
cgttcgctgg ttcccttttg atgtgcagca gtgcaaactg aagtttgggt cctggtccta       540
tggagggtgg tcactggacc tgcaaatgca agaggcagat atcagcagct atatccccaa       600
cggagaatgg gatctcatgg gaatccctgg caaaaggaat gagaagttct atgagtgctg       660
caaagagcca tacccagatg tcacctacac agtaaccatg cgccgtagga cactctacta       720
tggcctcaat ctgctcatcc cttgtgtact catttcagcc ctggctctgc tggtattctt       780
gctgcctgca gactctggag agaaaatctc tcttggaata actgtcttac tttctctgac       840
tgtcttcatg ctgcttgtgg ctgagatcat gccagcaaca tctgattctg cccttgat       900 agcacaatac ttcgccagca ccatgatcat cgtgggcctc tctgtagtgg tgacagtgat       960
tgtgctgaga tatcaccacc atgaccctga tggtggcaaa atgcctaagt ggaccagaat      1020
cattctcctg aactggtgtg catggtttct gcgcatgaag aggcccggag aggacaaggt      1080
gcggccagct tgtcagcaca agcctcggcg ctgcagcctg gccagtgtgg agctgagtgc      1140
aggtgctggg ccacccacca gcaatggcaa cctgctctac attggcttcc gaggcctgga      1200
gggcatgcac tgtgccccaa ctccagactc tgggtcgta tgtggccgtt tggcctgctc      1260
cccaacacat gatgagcacc tcatgcacgg tgcacacccc tctgatgggg accccgacct      1320
ggccaagatc ctggaggagg tccgctacat cgccaaccgc ttccgctgcc aggacgagag      1380
tgaggtgatc tgcagtgaat ggaagtttgc agcctgcgtg gtggaccgct tgtgcctcat      1440
ggccttttcg gtctttacca tcatctgtac catcggcatc ctcatgtcag ctccaaactt      1500
tgtggaggct gtgtccaaag actttgctta atgttatcaa gtaggaaatg cgcagataag      1560
aagagaatct ggagggtgag aattggggtc ctaactccac agtgtgataa atggaagaac      1620
tctgaggtat ccctgtagct gtcaatcttg agacttagtt ttctggttac tttaactgaa      1680
aagatctcag cagccttctg tttattcttc tctcccttat cactggcata gccttgtact      1740
cagcaggggc actacgtggt cgtttgtctg ctctggacag ccctatagga tagatcttag      1800
tggctcttgc agcccagtaa aagcctgtcc tgttggtggt gcatggaaac atgccccagt      1860
```

```
cctgggctca caagaattcg ctgtctgcct ttgctatgcg cagacccagg ctgaaaccaa    1920
tgcagagcag tccccactgg atccaccgca gcaactgcca tgaaaaagga aggcaaatac    1980
aaattcaaac tgcaaacttc tctgctagtt tctctgctag ttttcctgtg attcaactta    2040
catttctgtc tgtttatctg tctgtctatc tatctatcta tctatctatc tatctatcta    2100
tctatc                                                               2106
```

NUCLEIC ACIDS ENCODING FUNCTIONAL SPLICE VARIANTS OF THE α7 NICOTINIC ACETYLCHOLINE RECEPTOR SUBUNIT AND METHODS FOR PRODUCING THE ENCODED PROTEINS

CROSS-REFERENCE TO RELATED APPLICATIONS

The present application claims the benefit of U.S. Provisional Application No. 60/320,085, filed Apr. 4, 2003, and the benefit of U.S. Provisional Application No. 60/319,678, filed Nov. 8, 2002, which are hereby incorporated by reference herein in their entirety, including any figures, tables, nucleic acid sequences, amino acid sequences, or drawings.

The subject invention was made with government support under a research project supported by NIH Grant Number 1RO1HL63247. The U.S. government has certain rights in this invention.

BACKGROUND OF THE INVENTION

Nicotinic acetylcholine receptor channels (nAChRs) that contain the α7 gene product (α7-nAChRs) are one of the most abundant types of nicotinic receptors in the vertebrate nervous system. The α7-nAChRs differ from most neuronal nicotinic receptors in that they bind α-bungarotoxin (αBgt) with high affinity and have calcium permeability comparable to N-methyl-D-aspartate (NMDA) receptors. The α7-AChRs modulate various cell processes ranging from synaptic transmission to apoptosis. These receptors appear to be involved in learning and memory, and have been linked to pathophysiological conditions such as schizophrenia. Recent experiments have also shown that the β-amyloid peptide is a ligand for α7-nAChRs, suggesting that α7-nAChR function may be altered during Alzheimer's disease.

The α7 nicotinic acetylcholine receptor subunit was first cloned from chick brain and was later shown to form functional homomeric AChRs when expressed in *Xenopus* oocytes, and to contribute to functional nAChRs in native cells. However, the composition and stoichiometry of native α7-nAChRs remain to be confirmed, and differences exist in the pharmacological and biophysical properties of α7-nAChRs from different cell types. For example, whereas α7-AChRs in rat hippocampal neurons desensitize rapidly and bind αBgt in an irreversible manner, α7-nAChRs in mammalian autonomic neurons desensitize slowly and recover rapidly from αBgt blockade.

It has been proposed that the heterogeneity in α7-nAChRs may be due to cell-dependent expression of α7 subunit isoforms. This theory was supported by the observation that splice variations of the α7 subunit are detected in human brain and leukocytes. However, most of these α7 isoforms contain a premature stop codon, or form a truncated subunit that is not activated by acetylcholine. While various other ligand-gated ion channels such as 5-hydroxytryptamine 3 (5-HT3) and gamma aminobutyric acid (GABA) receptors have been shown to express functional splice variants with distinct properties, there is little indication that this type of diversity exists in nicotinic acetylcholine receptors.

SUMMARY OF THE INVENTION

The present invention relates to a splice variation of the α7 subunit gene that contributes to a unique nicotinic acetylcholine receptor (nAChR). The variant α7 subunit (also referred to herein as the α7-2 isoform or α7-2 splice variant) results from the incorporation of a novel exon into the α7 subunit transcript.

The nucleotide sequence encoding the α7-2 splice variant differs from the wild-type α7 subunit (also referred to herein as α7-1) in containing an 87 base pair insert that represents the incorporation of the novel exon (referred to herein as exon 4a) between exons 4 and 5 of the α7-1 gene product. The α7-2 splice variant is expressed in both peripheral and central neurons, and when expressed in *Xenopus* oocytes produces functional ACh-gated ion channels. The α7-2 variant has been identified in intracardiac ganglia and brain tissue.

The α7-2 splice variant exhibits unexpectedly different pharmacological and electrophysiological characteristics. The biophysical and pharmacological properties of the homomeric channel formed by α7-2 differ from those of homomeric α7-1-nAChRs and resemble those of the slowly desensitizing α7-nAChRs of rat autonomic neurons.

Accordingly, one aspect of the present invention is an isolated polynucleotide that encodes a variant of the wild-type nAChR α7 subunit, wherein the polynucleotide encodes a polypeptide comprising the amino acid sequence GCQLHFDQDLQNMLLREACAQAGEDLRVS (SEQ ID NO:15), or a functional fragment or homologue thereof. In one embodiment, the polynucleotide comprises exon 4a gggtgtcagttgcattgaccaagatctgcagaacatgcttctcagagaagcatgtgcacaggctggagaagatctaagagtcagt (SEQ ID NO:5). In another aspect, the present invention concerns a polypeptide comprising SEQ ID NO:15, or a functional fragment or homolog thereof. In other aspects, the present invention concerns an isolated nAChR comprising the α7-2 gene produce, and an isolated polynucleotide encoding the α7-2 nAChR.

In another aspect, the present invention concerns a recombinant vector comprising a polynucleotide of the invention is provided. In another aspect, the present invention concerns genetically modified host cells that have been transformed or transfected with vectors comprising a polynucleotide of the invention are provided. In another aspect, the present invention concerns methods of producing recombinant polypeptides for the treatment of neurological conditions (e.g., neurodegenerative processes), enzymatic function, affective disorders, and immunofunction, using such cells.

In another aspect, the present invention concerns agents (e.g., antisense polynucleotides, compounds), such as antagonists, which are useful in treating conditions such as neurological conditions (e.g., neurodegenerative processes), enzymatic function, affective disorders, and immunofunction. Methods of treating patients using these antisense polynucleotides and compounds are also provided.

In another aspect, the present invention pertains to methods and reagents for detecting the α7-2 splice variant.

In another aspect, the present invention is directed to a method of expressing a polynucleotide comprising the 4a exon, such as SEQ ID NO:5 or SEQ ID NO:14, in a cell. In one embodiment, a polynucleotide encoding the α7-2 variant subunit is expressed in the cell. In another embodiment, a polynucleotide encoding an nAChR comprising the α7-2 variant subunit is expressed in the cell.

In another aspect, the present invention is directed to a method of identifying agents that modulate the α7-2 subunit and receptors containing the subunit, and to a method of identifying cytoprotective or other therapeutic agents, using recombinant cells of the present invention.

BRIEF DESCRIPTION OF THE DRAWINGS

FIGS. 1A-1C demonstrate detection of multiple splice forms of the α7 neuronal nicotinic receptor subunit in rat intracardiac neurons. FIG. 1A shows results of RT-PCR amplification of RNA extracts from rat intracardiac ganglia using the α7 subunit-specific primers, α7-P1. Arrows point to the bands representing the conventional α7 gene product (α7-1) and the new sequence variant (α7-2). Standards are a 100 bp ladder and the 500 bp marker is indicated. FIGS. 1B and 1C show representations of the α7-1 subunit transcript (FIG. 1B) and other splice forms of the α7 subunit (FIG. 1C) detected in intrinsic cardiac neurons. Regions encoding the principal loops contributing to the acetylcholine (ACh) binding site and the transmembrane domains are marked relative to the exon structure. Deletions and the insertions resulting in the sequence variations are also shown in FIG. 1C.

FIG. 2 shows the nucleic acid sequence of the α7-2 splice variation (SEQ ID NO:2) and wild-type α7 gene (α7-1) (SEQ ID NO:3). The nucleotide sequence of the insert (SEQ ID NO:5), exon 4a, contributing to the α7-2 variant and flanking regions as amplified by primers α7-P1 are shown, aligned to the nucleotide and amino acid sequences of the α7-1 isoform (RATNARAD) (SEQ ID NO:3 and SEQ ID NO:4, respectively). Matching sequence is shown in white text and black highlight. The deduced amino acid sequence of the α7-2 splice variation is also provided (SEQ ID NO:1). The entire nucleotide sequence of the rat α7-1 gene, including non-coding regions and regions outside the primer amplified regions, is shown in SEQ ID NO:16.

FIG. 3 demonstrates identification of the novel exon in the α7 gene. PCR amplification of genomic extracts from rat liver (lanes 1 and 2) using α7-2 subunit-specific primers α7-P2 and α7-P3, respectively. Amplification of α7-2 cDNA (cDNA) using both the α7-P2 and α7-P3 primers. The right arrow indicates the predicted product size for α7-P3 amplification of α7-2 cDNA. The larger product represents product amplified by the forward primer of α7-P2 and the reverse primer of α7-P3. Standards are a 100 bp ladder and the 500 bp marker is indicated. Negative control (Neg. Cont.) represents PCR reaction using $H_2O$.

FIG. 4 shows the sequence of an intron separating exons 4 and 4a, with the sequence of the α7 gene (α7-1) (SEQ ID NO:3) aligned to the α7-2 isoform (α7-2) (SEQ ID NO:2). Matching sequence is shown in white test and black highlight. Consensus donor (gt) and acceptor (ag) sites are shown in italics and with gray highlight.

FIG. 5A shows results of RT-PCR amplification of RNA extracts from rat brain, intracardiac ganglia (ICG) and superior cervical ganglia (SCG) using the α7-2 subunit-specific primers, α7-P4. FIG. 5B shows results of RT-PCR amplification of cytoplasmic extract from a single isolated intrinsic cardiac neuron (ICG). Negative control was conducted using sample of extracellular solution collected near the cell shown here. Arrow indicates the predicted size for the α7-2 product (475 bp). Standards are a 100 bp ladder and the 500 bp marker is indicated.

FIGS. 6A and 6B show immunoblot detection of α7-2 expression in central and peripheral neurons. FIG. 6A shows immunoblot analysis of rat intracardiac ganglia (ICG), superior cervical ganglia (SCG) and brain detergent extracts using Ab 87. FIG. 6B shows immunoblot analysis of protein extracts from the indicated tissues either mock-depleted with rabbit-anti-rat IgG (Control) or immunodepleted with rabbit-anti-rat IgG and mAb 319 (Anti-α7). Tissues were probed for α7-2 expression using Ab 87. Each lane contained 8 μg of total protein. Protein size markers are indicated in kDa.

FIG. 7A shows currents recorded in response to rapid application of ACh (1 s) at the indicated concentrations from a voltage clamped oocyte (−70 mV) injected with α7-2 (left panel) or α7-1 (right panel) cRNA. FIG. 7B shows the concentration-response relationship for ACh-evoked currents in oocytes injected with α7-1 (•) or α7-2 (▼). Data represent mean±SEM with n=5 for both conditions. Lines represent best fit to the data using the Hill equation. $EC_{50}$ value and Hill coefficient were 278 μM and 1.8 for α7-1 and 2.4 μM and 1.2 for α7-2, respectively.

FIG. 8A shows ACh-evoked (100 μM) currents recorded from a voltage-clamped oocyte (−70 mV) injected with α7-2 cRNA in the absence (Control), presence of 50 nM αBgt (+αBgt) or following washout of the toxin for the indicated time. FIG. 8B shows a bar graph of peak current evoked at −70 mV by 100 μM ACh in the absence (Control), presence of 50 nM αBgt (+αBgt) and following 5 min washout of toxin (Wash). Currents are normalized to control (n=4). FIG. 8C shows currents elicited from a single oocyte injected with α7-2 cRNA in response to 1 s (upper trace) of 5 s (lower trace) application of 100 μM ACh. Dashed lines represent best-fit to the data using a single exponential function, with τ=1.2 s for both conditions. FIG. 8D shows superimposed ACh-evoked (1 s application) currents recorded from two oocytes injected with α7-1 (300 μM ACh) and α7-2 (3 μM ACh) cRNA, respectively. The responses have been scaled to the current amplitude of α7-1. For comparison, the rapid decay phase for each response are scaled to their respective maximums and overlaid in the insert.

BRIEF DESCRIPTION OF SEQUENCES

Figure 5A:
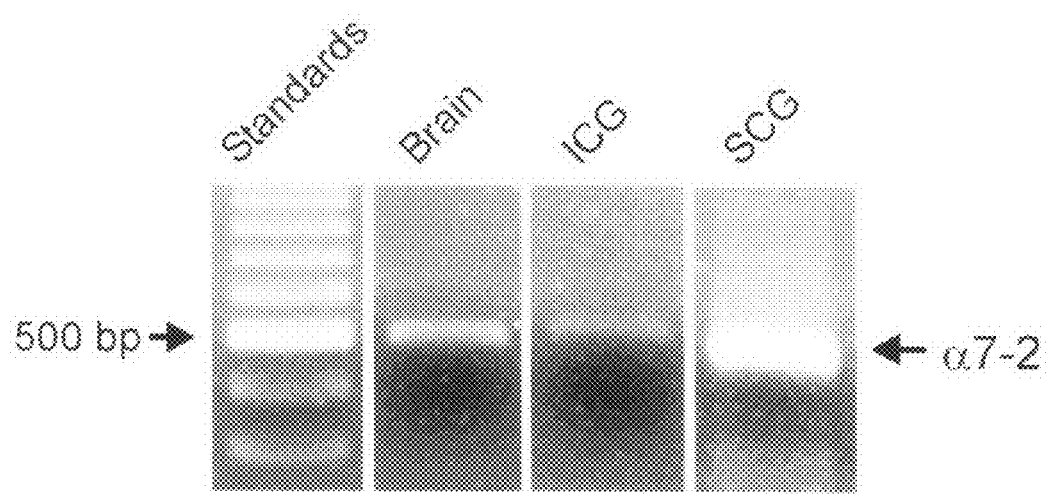
FIGS. 5A and 5B show that the α7-2 splice variant is found in brain and in both sympathetic and parasympathetic neurons.

SEQ ID NO:1 is the deduced amino acid sequence of the rat α7-2 subunit splice variant (FIG. 2).

SEQ ID NO:2 is the nucleotide sequence of the rat α7-2 subunit splice variant (FIG. 2).

SEQ ID NO:3 is the nucleotide coding sequence of the rat wild-type α7 subunit gene (α7-1) (FIG. 2).

SEQ ID NO:4 is the amino acid sequence of the rat wild-type α7 (α7-1) subunit (FIG. 2).

SEQ ID NO:5 is the nucleotide sequence of the rat α7-2 variant 4a exon (FIG. 2).

SEQ ID NO:6 is forward α7-P1 primer.

SEQ ID NO:7 is the reverse α7-P1 primer.

SEQ ID NO:8 is the forward α7-P2 primer.

SEQ ID NO:9 is the reverse α7-P2 primer.

SEQ ID NO:10 is the forward α7-P3 primer.

SEQ ID NO:11 is the reverse α7-P3 primer.

SEQ ID NO:12 is the forward α7-P4 primer.

SEQ ID NO:13 is the reverse α7-P4 primer.

SEQ ID NO:14 is the nucleotide sequence of exon 4A of the mouse α7-2 subunit.

SEQ ID NO:15 is the deduced amino acid sequence of the rat α7-2 variant 4a exon (FIG. 2).

SEQ ID NO:16 is the nucleotide sequence of the rat wild-type α7-1 subunit, including non-coding regions at the 5' and 3' ends.

DETAILED DISCLOSURE

The present study shows the first evidence for a functional splice variant of a nicotinic receptor subunit that contributes to a unique receptor. The α7-2 isoform of the α7 nicotinic receptor subunit contains an 87 base pair insert that represents the incorporation of a novel exon (exon 4a) between exons 4 and 5 of the conventional α7 gene product (α7-1). The α7-2 splice variant is expressed in both peripheral and central neurons, and when expressed in *Xenopus* oocytes produces functional ACh-gated ion channels. The biophysical and pharmacological properties of the homomeric channel formed by α7-2 differ from those of homomeric α7-1-nAChRs and resemble those of the slowly desensitizing α7-nAChRs of rat autonomic neurons.

Fast synaptic transmission in mammalian autonomic ganglia is mediated primarily by nicotinic receptors, and one of the most abundant nicotinic receptor subtypes in these neurons contains the α7 subunit (α7-nAChRs). Unlike α7-nAChRs expressed in other cells, the predominant α7-nAChRs subtype found in rat intracardiac and superior cervical ganglion neurons exhibits a slow rate of desensitization and is reversibly blocked by α-bungarotoxin.

The present inventors have discovered that rat autonomic neurons contain a sequence variant of the α7 subunit that incorporates a novel 87 bp cassette exon in the N-terminus of the receptor that preserves the reading frame of the transcript. This α7 isoform was detected using RT-PCR techniques in neonatal rat brain and intracardiac and superior cervical ganglion neurons. Immunoblot experiments using a polyclonal antibody directed against the deduced amino acid sequence of the α7-2 insert showed a pattern of expression consistent with α7-2 subunit mRNA distribution. Moreover, the α7-2 subunit could be immunodepleted from protein extracts by solid-phase immunoprecipitation techniques using the anti-α7 monoclonal antibody, mAb 319. The α7-2 subunit was shown to form functional homomeric ion channels that were activated by acetylcholine and blocked by α-bungarotoxin when expressed in *Xenopus* oocytes. This α7 isoform exhibited a slow rate of desensitization, and inhibition of these channels by α-bungarotoxin reversed rapidly following washout of drug. Taken together, these data indicate that the α7-2 subunit is capable of forming functional αBgt-sensitive AChRs that resemble the α7-AChRs previously identified in rat autonomic neurons. Furthermore, the distribution of the α7-2 isoform is not limited to peripheral neurons.

The term "AChR", as used herein, refers to a receptor for the neurotransmitter acetylcholine ("Ach"). AChRs are broadly subclassified as nicotinic or muscarinic. These types differ in their pharmacology, structures, and signal transduction mechanisms.

The term "nAChR", as used herein, refers to a nicotinic acetylcholine receptor. Although nAChRs of various subunit structures are best known in muscle cells, neurons, and chromaffin cells, they are not necessarily excluded from other cells types (e.g., glial cells, mast cells, blood cells, fibroblasts, etc.).

The term "nAChR subunit", as used herein, refers to a proteinaceous molecule that can combine with other such molecules in the formation of a nAChR. For example, the muscle nAChR is believed to be a pentamer comprised of four types of transmembrane subunit: two α1 subunits, one β1 subunit, one δ subunit and one γ or ε subunit depending upon the nAChR form. Neuronal nAChRs analogously are also thought to be pentameric and comprised of related but different subunits. At present, eight neuronal α subunits (α2-α9) and three neuronal β subunits (β2-β4) have been isolated. Some neuronal nAChRs appear to require at least one α subunit and at least one β subunit for a functional complex (e.g., exhibiting ion channel response to ACh or other agonists). Some subunits, however, may self-assemble to form "homooligomeric" nAChR, as in the case of α7 nAChR in *Xenopus* oocytes and in transfected mammalian cells. Although the combination of nAChR subunits with subunits related to other types of receptor (e.g., other classes of ligand-gated ion channel) has not been demonstrated, such combinations are possible and contemplated within the scope of the present invention.

The term "wild-type" (WT), as used herein, refers to the typical, most common or conventional form as it occurs in nature. The human wild-type α7 nAChR was described by Doucette-Stamm et al. (*Drug Dev. Res.* 30: 252-256, 1993). The rat and mouse wild-type α7 nAChRs were described by Khiroug, S. S., et al. (*J. Physiol.* (*Lond.*) 540 (Pt 2), 425-434, 2002) (NCBI Accession No. L31629); and Orr-Urtreger, A., et al. (*Genomics* 26 (2), 399-402, 1995) (NCBI Accession No. L37663), respectively.

The term "nicotinic cholinergic agonist", as used herein, refers to an agent that binds to and activates a nicotinic acetylcholine receptor. By "activates" is intended the elicitation of one or more pharmacological, physiological, or electrophysiological responses. Such a response includes, but is not limited to, cell membrane depolarization and increased permeability to $Ca_2^+$ other cations.

The term "nicotinic cholinergic antagonist", as used herein, refers to a substance that binds to a nicotinic acetylcholine receptor and prevents agonists from activating the receptor. Pure antagonists do not activate the receptor, but some substances may have mixed agonist and antagonist properties. Nicotinic cholinergic channel blockers block the ability of agonists to elicit current flow through the nicotinic acetylcholine receptor channel, but do so by blocking the channel rather than by preventing agonists from binding to and activating the receptor.

The term "nicotinic cholinergic modulator", as used herein, refers to an agent that influences the activity of the nicotinic acetylcholine receptor through interaction at one or more sites other than the classic agonist binding site. The modulator may itself increase or decrease receptor activity, or may influence agonist activity (for example, potentiating responses) without itself eliciting an overt change in channel current. A single agent can have different properties at different nicotinic acetylcholine receptor subtypes, for example, being an agonist at one receptor and antagonist at another, or an antagonist at one and a channel blocker at another.

The term "nAChR regulator", as used herein, refers to an agent that may act as an agonist, antagonist, channel blocker or modulator.

The term "polynucleotide", as used herein, refers to a polymeric form of nucleotides of any length, either ribonucleotides or deoxyribonucleotides. This term refers only to the primary structure of the molecule. Thus, the term includes double-stranded and single-stranded DNA, as well as double-stranded and single-stranded RNA. It also includes modifications, such as by methylation and/or by capping, and unmodified forms of the polynucleotide.

The term "variant", as used herein, refers to an oligonucleotide sequence which differs from the related wild-type sequence in one or more nucleotides. Such a variant oligonucleotide is expressed as a protein variant which, as used herein, indicates a polypeptide sequence that differs from the wild-type polypeptide in the substitution, insertion or deletion of one or more amino acids. The variant polypeptide differs in primary structure (amino acid sequence), but may or may not differ significantly in secondary or tertiary structure or in function relative to the wild-type. In the case of the α7-2 variant subunit if the present invention, a novel exon (exon 4a) is incorporated between exons 4 and 5 of the α7-2 subunit gene.

The term "mutant", as used herein, generally refers to an organism or a cell displaying a new genetic character or phenotype as the result of change in its gene or chromosome. In some instances, however, the term "mutant" may be used in reference to a variant protein or oligonucleotide and "mutation" may refer to the change underlying the variant.

The terms "polypeptide" and "protein" are used interchangeably herein and indicate a molecular chain of amino acids of any length linked through peptide bonds. Thus, peptides, oligopeptides, and proteins are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide.

The nucleotide sequences comprising the 4a exon, or encoding the α7-2 variant subunit, or encoding the α7-2 variant nAChR used in the subject invention include "homologous" or "modified" nucleotide sequences. Homologous nucleic acid sequences will be understood to include any nucleotide sequence obtainable by mutagenesis according to techniques well known to persons skilled in the art, and exhibiting modifications in relation to the normal sequences. For example, mutations in the regulatory and/or promoter sequences for the expression of a polypeptide that result in a modification of the level of expression of a polypeptide according to the invention provide for a "modified nucleotide sequence". Likewise, substitutions, deletions, or additions of nucleic acid to the polynucleotides of the invention provide for "homologous" or "modified" nucleotide sequences. In various embodiments, "homologous" or "modified" nucleic acid sequences have substantially the same biological function in vitro and/or in vivo as the native (naturally occurring) α7-2 variant of the present invention. The function of homologues of the invention can be assessed by a number of methods known for assessing nAChR receptor function known in the art, including those disclosed herein. For example, function of homologues can be determined in the Xenopus oocyte by a variety of electrophysiological techniques including intracellular voltage recording, two-electrode voltage clamp, patch clamp methods, and the like. A "homologous" or "modified" nucleotide sequence will also be understood to include a splice variant of the polynucleotides of the instant invention or any nucleotide sequence encoding a "modified polypeptide" as defined below. A "homologues" or "modified" nucleotide or amino acid sequence will also be understood to include mammalian homologues of the nucleotide sequences and amino acid disclosed herein.

Homologues of the present invention include those sequences having "functionally conservative mutations" and/ or "structurally conservative mutations." The phrase "functionally conservative mutation", as used herein, intends a change in a polynucleotide encoding a derivative polypeptide in which the activity is not substantially altered compared to that of the polypeptide from which the derivative is made. Such derivatives may have, for example, amino acid insertions, deletions, or substitutions in the relevant molecule that do not substantially affect its properties (see Table 1). Functionally conservative mutants of the amino acid sequence of SEQ ID NO:1 are encompassed by the present invention.

The phrase "structurally conservative mutant", as used herein, refers to a polynucleotide containing changes in the nucleic acid sequence but encoding a polypeptide having the same amino acid sequence as the polypeptide encoded by the polynucleotide from which the degenerate variant is derived. This can occur because a specific amino acid may be encoded by more than one codon (sequence of three nucleotides). Structurally conservative mutants of the nucleic acid sequences of SEQ ID NO:2, SEQ ID NO:5, and SEQ ID NO:14 are encompassed by the present invention, for example.

A homologous nucleotide sequence, for the purposes of the present invention, encompasses a nucleotide sequence having a percentage identity with the bases of the nucleotide sequences of between at least (or at least about) 20.00% to 99.99% (inclusive). The aforementioned range of percent identity is to be taken as including, and providing written description and support for, any fractional percentage, in intervals of 0.01%, between 20.00% and 99.99%. These percentages are purely statistical and differences between two nucleic acid sequences can be distributed randomly and over the entire sequence length.

In various embodiments, homologous sequences exhibiting a percentage identity with the bases of the nucleotide sequences of the present invention can have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the polynucleotide sequences of the instant invention. Homologous nucleotide and amino acid sequences include mammalian homologues of the rat and mouse α7-2 4a exon, mammalian homologues of the rat and mouse α7-2 variant subunit, and mammalian homologues of the rat and mouse α7-2 variant nAChR. In a specific embodiment, the mammalian homologue is nucleotide and amino acid sequences of the human α7-2 4a exon, the human α7-2 variant subunit, and the human α7-2 variant nAChR.

The α7-2 variant homologues of the present invention include polypeptides containing, as a primary amino acid sequence, all or part of an exemplified α7-2 variant polypeptide sequence. The α7-2 variant homologues thus include α7-2 variant polypeptides having conservative substitutions, i.e., altered sequences in which functionally equivalent amino acid residues are substituted for residues within the sequence resulting in a peptide which is biologically active. For example, one or more amino acid residues within the sequence can be substituted by another amino acid of a similar polarity which acts as a functional equivalent, resulting in a silent alteration. In one aspect of the present invention, conservative substitutions for an amino acid within the sequence may be selected from other members of the class to which the amino acid belongs (see Table 1). Conservative substitutions also include substitutions by amino acids having chemically modified side chains which do not eliminate the biological function of the resulting α7-2 variant homologue.

TABLE 1

| Class of Amino Acid | Examples of Amino Acids |
|---|---|
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Both protein and nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman *Proc. Natl. Acad. Sci. USA*, 1988, 85(8):2444-2448; Altschul et al. *J. Mol. Biol.*, 1990, 215(3): 403-410; Thompson et al. *Nucleic Acids Res.*, 1994, 22(2): 4673-4680; Higgins et al. *Methods Enzymol.*, 1996, 266:383-402; Altschul et al. *J. Mol. Biol.*, 1990, 215(3):403-410; Altschul et al. *Nature Genetics*, 1993, 3:266-272).

Identity and similarity of related nucleic acid molecules and polypeptides can be readily calculated by known methods. Such methods include, but are not limited to, those described in Computational Molecular Biology, Lesk, A. M., ed., Oxford University Press, New York, 1988; York (1988); Biocomputing: Informatics and Genome Projects, Smith, D. W., ed., Academic Press, New York, 1993; York (1993); Computer Analysis of Sequence Data, Part 1, Griffin, A. M., and Griffin, H. G., eds., Humana Press, New Jersey, 1994; Jersey (1994); Sequence Analysis in Molecular Biology, von Heinje, G., Academic Press, 1987; Press (1987); Sequence Analysis Primer, Gribskov, M. and Devereux, J., eds., M. Stockton Press, New York, 1991; York (1991); and Carillo et al., SIAM J. Applied Math., 48:1073 (1988).

The methods, vectors, and compositions of the present invention can utilize functional fragments of nucleic acid sequences encoding the 4a exon, the α7-2 variant subunit and α7-2 variant nAChR disclosed herein.

Representative fragments of the nucleotide sequences according to the invention will be understood to mean any polynucleotide fragment having at least 8 or 9 consecutive nucleotides, preferably at least 12 consecutive nucleotides, and still more preferably at least 15 or at least 20 consecutive nucleotides of the sequence from which it is derived. The upper limit for such fragments is one nucleotide less than the total number of nucleotides found in the full-length sequence (or, in certain embodiments, of the full length open reading frame (ORF) identified herein).

In other embodiments, depending upon the relevant full-length sequence from which they are derived, fragments can comprise consecutive nucleotides of 8, 9, 1, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, and up to one nucleotide less than the full-length 4a exon, α7-2 variant subunit, or α7-2 variant nAChR disclosed herein.

It is also well known in the art that restriction enzymes can be used to obtain functional fragments of the nucleic acid sequences. For example, Bal31 exonuclease can be conveniently used for time-controlled limited digestion of DNA (commonly referred to as "erase-a-base" procedures). See, for example, Maniatis et al. *Molecular Cloning: A Laboratory Manual*, 1982, Cold Spring Harbor Laboratory, New York; Wei et al. *J. Biol. Chem.*, 1983, 258:13006-13512.

The methods, vectors, and compositions of the present invention can utilize amino acid sequences that are functional fragments of the full-length 4a exon encoded polypeptide, α7-2 variant subunit polypeptide, or α7-2 variant nAChR polypeptide disclosed herein.

Representative fragments of the polypeptides according to the invention will be understood to mean any polypeptide fragment having at least 8 or 9 consecutive amino acids, preferably at least 12 amino acids, and still more preferably at least 15 or at least 20 consecutive amino acids of the polypeptide sequence from which it is derived. The upper limit for such fragments is one amino acid less than the total number of amino acids found in the full-length sequence.

In other embodiments, depending upon the relevant full-length sequence from which they are derived, fragments of the polypeptides can comprise consecutive amino acids of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, and up to one amino acid less than the full-length 4a exon encoded polypeptide, the α7-2 variant subunit polypeptide, or the α7-2 variant nAChR polypeptide disclosed herein. Fragments of polypeptides can be any portion of the full-length amino acid sequence (including human or non-human mammalian homologues) that exhibit functional activity, e.g., a C-terminally or N-terminally truncated version, or an intervening portion of the full-length sequence.

The terms "recombinant host cells", "host cells", "cells", "cell lines", "cell cultures", and other such terms denoting microorganisms or higher eukaryotic cell lines cultured as unicellular entities refer to cells which can be, or have been, used as recipients for recombinant vectors or other transfer DNA, immaterial of the method by which the DNA is introduced into the cell or the subsequent disposition of the cell. The terms include the progeny of the original cell that has been transfected. Cells in primary culture as well as cells such as oocytes also can be used as recipients.

The term "genetic modification" as used herein refers to the stable or transient alteration of the genotype of a cell of the subject invention by intentional introduction of exogenous nucleic acids by any means known in the art (including for example, direct transmission of a polynucleotide sequence from a cell or virus particle, transmission of infective virus particles, and transmission by any known polynucleotide-bearing substance) resulting in a permanent or temporary alteration of genotype. The nucleic acids may be synthetic, or naturally derived, and may contain genes, portions of genes, or other useful polynucleotides in addition to those encoding α7-2 4a exon encoded polypeptides, the α7-2 subunit polypeptide, or the α7-2 nACh receptor polypeptide. A translation initiation codon can be inserted as necessary, making methionine the first amino acid in the sequence.

The term "vector" is used to refer to any molecule (e.g., nucleic acid, plasmid, or virus) usable to transfer coding sequence information (e.g., nucleic acid sequence encoding the α7-2 4a exon, the α7-2 subunit, or the α7-2 nACh receptor), such as to a host cell. A vector typically includes a replicon in which another polynucleotide segment is attached, such as to bring about the replication and/or expression of the attached segment. The term includes expression vectors, cloning vectors, and the like. Thus, the term includes gene expression vectors capable of delivery/transfer of exogenous nucleic acid sequences into a host cell. The term "expression vector" refers to a vector that is suitable for use in a host cell (e.g., a patient's cell) and contains nucleic acid sequences which direct and/or control the expression of exogenous nucleic acid sequences. Expression includes, but is not limited to, processes such as transcription, translation, and RNA splicing, if introns are present. Nucleic acid sequences can be modified according to methods known in the art to provide optimal codon usage for expression in a particular expression system. The vector may include elements to control targeting, expression and transcription of the nucleic acid sequence in a cell selective manner as is known in the art. It should be noted that often the 5'UTR and/or 3'UTR of the gene may be replaced by the 5'UTR and/or 3'UTR of the expression vehicle. The vector can include a promoter for controlling transcription of the exogenous material and can be either a constitutive or inducible promoter to allow selective transcription. The expression vector can also include a selection gene.

A "coding sequence" is a polynucleotide sequence that is transcribed into mRNA and/or translated into a polypeptide. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences. Variants or analogs may be prepared by the deletion of a portion of the coding sequence, by insertion of a sequence, and/or by substitution of one or more nucleotides within the sequence. Techniques for modifying nucleotide sequences, such as site-directed mutagenesis, are well known to those skilled in the art (See, e.g., Sambrook et al., Molecular Cloning: A Laboratory Manual, Second Edition, 1989; DNA Cloning, Vols. I and II, D. N. Glover ed., 1985). Optionally, the polynucleotides of the present invention, and composition and methods of the invention that utilize such polynucleotides, can include non-coding sequences.

The term "operably-linked" is used herein to refer to an arrangement of flanking control sequences wherein the flanking sequences so described are configured or assembled so as to perform their usual function. Thus, a flanking control sequence operably-linked to a coding sequence may be capable of effecting the replication, transcription and/or translation of the coding sequence under conditions compatible with the control sequences. For example, a coding sequence is operably-linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence, and the promoter sequence can still be considered "operably-linked" to the coding sequence. Each nucleotide sequence coding for a polypeptide will typically have its own operably-linked promoter sequence.

The terms "transfection" and "transformation" are used interchangeably herein to refer to the insertion of an exogenous polynucleotide into a host cell, irrespective of the method used for the insertion, the molecular form of the polynucleotide that is inserted, or the nature of the cell (e.g., prokaryotic or eukaryotic). The insertion of a polynucleotide per se and the insertion of a plasmid or vector comprised of the exogenous polynucleotide are included. The exogenous polynucleotide may be directly transcribed and translated by the cell, maintained as a nonintegrated vector, for example, a plasmid, or alternatively, may be stably integrated into the host genome.

The term "isolated", as used herein, when referring to a polynucleotide or a polypeptide, means that the indicated molecule is present in the substantial absence of other similar biological macromolecules. The term "isolated" as used herein means that at least 75 wt. %, more preferably at least 85 wt. %, more preferably still at least 95 wt. %., and most preferably at least 98 wt. % of a composition is the isolated polynucleotide or polypeptide. An "isolated polynucleotide" that encodes a particular polypeptide refers to a polynucleotide that is substantially free of other nucleic acid molecules that do not encode the subject polypeptide; however, the molecule may include functionally and/or structurally conservative mutations as defined herein.

The term "test sample", as used herein, refers to a component of an patient's body which is a source of the α7-2 subunit. These test samples include biological samples which can be evaluated by the methods of the present invention described herein and include body fluids such as whole blood, tissues and cell preparations.

The following single-letter amino acid abbreviations are used throughout the text: Alanine: A; Arginine: R; Asparagine: N; Aspartic acid: D; Cysteine: C; Glutamine: Q; Glutamic acid: E; Glycine: G; Histidine: H; Isoleucine: I; Leucine: L; Lysine: K; Methionine: M; Phenylalanine: F; Proline: P; Serine: S; Threonine: T; Tryptophan: W; Tyrosine: Y; and Valine: V.

A variant α7 subunit (i.e., an α7-2 variant), a polynucleotide encoding the variant subunit, and methods of making the variant subunit are provided herein. The invention includes not only the variant subunit but also methods for screening compounds using the variant subunit and cells expressing the variant subunit. Further, polynucleotides and antibodies which can be used in methods for detection of the variant subunit, as well as the reagents useful in these methods, are provided. Compounds and polynucleotides useful in regulating the variant and its expression also are provided as disclosed hereinbelow.

In one embodiment, the polynucleotide of the invention encodes an α7 subunit variant in which an additional exon (exon 4a) exists between exons 4 and 5 of the normal, wild-type α7-1 subunit gene product. In specific embodiments, the additional exon comprises the nucleotide sequence of SEQ ID NO:5 (rat) or SEQ ID NO:14 (mouse), or functional fragments or homologues of SEQ ID NO:5 or SEQ ID NO:14, such as mammalian homologues.

A polynucleotide encoding the 4a exon or the α7-2 variant subunit can be derived from genomic or cDNA, prepared by synthesis, or by a combination of techniques. The polynucleotide can then be used to express the α7-2 variant subunit or as a template for the preparation of RNA using methods well known in the art (see, Sambrook et al., Molecular Cloning: A Laboratory Manual, Second Edition, 1989).

One method for obtaining the desired polynucleotide involves isolating cDNA encoding the wild-type α7 nAChR subunit (also referred to herein as the α7-1 subunit) as described by Doucette-Stamm et al. *Drug Dev. Res.,* 1993, 30: 252-256. The wild-type cDNA thus obtained can then be modified and amplified using the polymerase chain reaction ("PCR") and primer sequences designed to obtain the DNA encoding the α7-2 variant subunit. More particularly, PCR employs short oligonucleotide primers (generally 10-20 nucleotides in length) that match opposite ends of a desired sequence within the wild-type DNA molecule. The sequence between the primers need not be known. The initial template can be either RNA or DNA. If RNA is used, it is first reverse-transcribed to cDNA. The cDNA is then denatured, using well known techniques such as heat, and appropriate oligonucleotide primers are added in molar excess.

The primer can be made specific by keeping primer length and base composition within relatively narrow limits, and by keeping the mutant base or bases corresponding to exon 4a centrally located (Zoler et al. (1983) *Meth. Enzymol.* 100: 468). Primer extension is effected using DNA polymerase in the presence of deoxynucleotide triphosphates or nucleotide analogs. The resulting product includes the respective primers at their 5'-termini, covalently linked to the newly synthesized complements of the original strands. The replicated molecule is again denatured, hybridized with primers, and so on, until the product is sufficiently amplified. Such PCR methods are described in the art, e.g., U.S. Pat. Nos. 4,965,188; 4,800,159; 4,683,202; 4,683,195; incorporated herein by reference in their entireties. The product of the PCR is cloned and the clones containing the mutated DNA, derived by segregation of the primer extended strand, selected. Selection can be accomplished using the mutant primer as a hybridization probe.

Alternatively, the wild-type DNA may be obtained from an appropriate DNA library. DNA libraries may be probed using the procedure described by Grunstein et al. (*Proc. Natl. Acad. Sci. USA* 73:3961, 1975).

Alternatively, the α7-2 variant subunit can be generated using an RT-PCR (reverse transcriptase-polymerase chain reaction) approach starting with RNA. For example, single-stranded cDNA is synthesized from human RNA (approx. 1.5 μg) as the template using standard reverse transcriptase procedures. Next, the cDNA is amplified in two segments and the mutation is introduced using PCR and two pairs of primers. For example, the internal primers are designed to carry one or more codons of the 4a exon. The products of the two PCR reactions are combined using the 3' and 5' end primers to re-amplify the full-length coding sequence of the α7-2 variant subunit.

Synthetic oligonucleotides may be prepared using an automated oligonucleotide synthesizer such as that described by Warner (*DNA* 3:401, 1984). If desired, the synthetic strands may be labelled with $^{32}P$ by treatment with polynucleotide kinase in the presence of $_{32}P$-ATP, using standard conditions for the reaction. DNA sequences, including those isolated from genomic or cDNA libraries, may be modified by known methods which include site-directed mutagenesis as described by Zoller (*Nucleic Acids Res.* 10:6487, 1982). Briefly, the DNA to be modified is packaged into phage as a single stranded sequence, and converted to a double stranded DNA with DNA polymerase using, as a primer, a synthetic oligonucleotide complementary to the portion of the DNA to be modified, and having the desired modification included in its own sequence. Culture of the transformed bacteria, which contain replications of each strand of the phage, are plated in agar to obtain plaques. Theoretically, 50% of the new plaques contain phage having the mutated sequence, and the remaining 50% have the original sequence. Replicates of the plaques are hybridized to labelled synthetic probe at temperatures and conditions suitable for hybridization with the correct strand, but not with the unmodified sequence. The sequences which have been identified by hybridization are recovered and cloned. Alternatively, it may be necessary to identify clones by sequence analysis if there is difficulty in distinguishing the variant from wild-type by hybridization. In any case, the DNA can be sequence-confirmed.

Once produced, the DNA may then be incorporated into a cloning vector or an expression vector for replication in a suitable host cell. Vector construction employs methods known in the art. Generally, site-specific DNA cleavage is performed by treating with suitable restriction enzymes under conditions which generally are specified by the manufacturer of the commercially available enzymes. After incubation with the restriction enzyme, protein is removed by extraction and the DNA recovered by precipitation. The cleaved fragments may be separated using, for example, polyacrylamide or agarose gel electrophoresis methods, according to methods known by those of skill in the art.

Sticky end cleavage fragments may be blunt ended using *E. coli* DNA polymerase 1 (Klenow) in the presence of the appropriate deoxynucleotide triphosphates (dNTPs) present in the mixture. Treatment with S1 nuclease also may be used, resulting in the hydrolysis of any single stranded DNA portions.

Ligations are performed using standard buffer and temperature conditions using T4 DNA ligase and ATP. Alternatively, restriction enzyme digestion of unwanted fragments can be used to prevent ligation.

Standard vector constructions can include specific antibiotic resistance elements. Ligation mixtures are transformed into a suitable host, and successful transformants selected by antibiotic resistance or other markers. Plasmids from the transformants can then be prepared according to methods known to those in the art usually following a chloramphenicol amplification as reported by Clewell et al. (*J. Bacteriol.* 110:667, 1972) may be added. The DNA is isolated and analyzed usually by restriction enzyme analysis and/or sequencing. Sequencing may be by the well-known dideoxy method of Sanger et al. (*Proc. Natl. Acad. Sci. USA* 74:5463, 1977) as further described by Messing et al. (*Nucleic Acid Res.* 2:309, 1981), or by the method reported by Maxam et al. (*Meth. Enzymol.* 65:499, 1980). Problems with band compression, which are sometimes observed in GC rich regions, are overcome by use of, for example, T-deazoguanosine or inosine, according to the method reported by Barr et al. (*Biotechniques* 4:428, 1986).

Host cells can be genetically modified with the vectors of the present invention which may be a cloning vector or an expression vector. The vector may be in the form of a plasmid, a viral particle, a phage, etc. The genetically modified host cells can be cultured in conventional nutrient media modified as appropriate for activating promoters, selecting transformants/transfectants or amplifying the subunit-encoding polynucleotide. The culture conditions, such as temperature, pH and the like, generally are similar to those previously used with the host cell selected for expression, and will be apparent to those of skill in the art.

Both prokaryotic and eukaryotic host cells may be used for expression of desired coding sequences when appropriate control sequences (e.g., promoter sequences) that are compatible with the designated host are used. For example, among prokaryotic hosts, *Escherichia coli* is frequently used. Also, for example, expression control sequences for prokaryotes include but are not limited to promoters, optionally containing operator portions, and ribosome binding sites. Transfer vectors compatible with prokaryotic hosts can be derived from, for example, the plasmid pBR322 that contains operons conferring ampicillin and tetracycline resistance, and the various pUC vectors, that also contain sequences conferring antibiotic resistance markers. These markers may be used to obtain successful transformants by selection. Commonly used prokaryotic control sequences include but are not limited to the lactose operon system (Chang et al. *Nature* 198:1056, 1977), the tryptophan operon system (reported by Goeddel et al. (*Nucleic Acid Res.* 8:4057, 1980) and the lambda-derived P1 promoter and N gene ribosome binding site (Shimatake et al. *Nature* 292:128, 1981), the hybrid Tac promoter (De Boer et al. *Proc. Natl. Acad. Sci. USA* 292:128, 1983) derived from sequences of the trp and lac UV5 promoters. The foregoing systems are particularly compatible with *E. coli*; however, other prokaryotic hosts such as strains of *Bacillus* or *Pseudomonas* may be used if desired.

Eukaryotic hosts include yeast and mammalian cells in culture systems. *Pichia pastoris, Saccharomyces cerevisiae* and *S. carlsbergensis* are commonly used yeast hosts. Yeast-compatible vectors carry markers that permit selection of successful transformants by conferring protrophy to auxotrophic mutants or resistance to heavy metals on wild-type strains. Yeast compatible vectors may employ the 2-μ origin of replication (Broach et al. *Meth. Enzymol.* 101:307, 1983), the combination of CEN3 and ARS1 or other means for assuring replication, such as sequences that will result in incorporation of an appropriate fragment into the host cell genome. Control sequences for yeast vectors are known in the art and include but are not limited to promoters for the synthesis of glycolytic enzymes, including the promoter for 3-phosphoglycerate kinase. (See, for example, Hess et al. *J. Adv. Enzyme Reg.* 7:149, 1968; Holland et al. *Biochemistry* 17:4900, 1978; and Hitzeman *J. Biol. Chem.* 255:2073, 1980). For example, some useful control systems are those that comprise the glyceraldehyde-3-phosphate dehydrogenase (GAPDH) promoter or alcohol dehydrogenase (ADH) regulatable promoter, terminators also derived from GAPDH, and, if secretion is desired, leader sequences from yeast alpha factor. In addition, the transcriptional regulatory region and the transcriptional initiation region which are operably linked may be such that they are not naturally associated in the wild-type organism.

Mammalian cell lines available as hosts for expression are known in the art and are available from depositories such as the American Type Culture Collection. These include but are not limited to HeLa cells, human embryonic kidney (HEK) cells, Chinese hamster ovary (CHO) cells, baby hamster kidney (BHK) cells, and others. Suitable promoters for mammalian cells also are known in the art and include viral promoters such as that from Simian Virus 40 (SV40), Rous sarcoma virus (RSV), adenovirus (ADV), bovine papilloma virus (BPV) and cytomegalovirus (CMV). Mammalian cells also may require terminator sequences and poly A addition sequences; enhancer sequences which increase expression also may be included, and sequences which cause amplification of the gene also may be desirable. These sequences are known in the art. Vectors suitable for replication in mammalian cells may include viral replicons, or sequences which ensure integration of the appropriate sequences encoding the 4a exon or α7-2 variant subunit into the host genome. An example of such a mammalian expression system is described in Gopalakrishnan et al. *Eur. J. Pharmacol.-Mol. Pharmacol.* 290: 237-246, 1995).

Other eukaryotic systems available as hosts for expression are also known, as are methods for introducing polynucleotides into such systems, such as amphibian cells using methods described in Briggs et al. (*Neuropharmacol.* 34:583-590, 1995), insect cells using methods described in Summers and Smith, Texas Agricultural Experiment Station Bulletin No. 1555 (1987), and the like.

The baculovirus expression system can be used to generate high levels of recombinant proteins in insect host cells. The baculovirus expression system allows for high level of protein expression, while post-translationally processing the protein in a manner similar to mammalian cells. These expression systems use viral promoters that are activated following baculovirus infection to drive expression of cloned genes in the insect cells (O'Reilly et al. (1992) Baculovirus Expression Vectors: A Laboratory Manual, IRL/Oxford University Press).

Transfection may be by any known method for introducing polynucleotides into a host cell, including packaging the polynucleotide in a virus and transducing a host cell with the virus, by direct uptake of the polynucleotide by the host cell, and the like, which methods are known to those skilled in the art. The transfection procedures selected depend upon the host to be transfected.

The expression of the polynucleotide encoding the 4a exon or α7-2 variant subunit may be detected by use of a radioligand selective for the receptor. For example, for the nicotinic cholinergic receptor, such a ligand may be $[^{125}I]$α-bungarotoxin. However, any radioligand binding technique known in the art may be used to detect the receptor subunit (see, e.g., Winzor et al. (1995) Quantitative Characterization of Ligand Binding, Wiley-Liss, Inc., N.Y.). Alternatively, expression can be detected by utilizing antibodies or functional measurements which are well known to those skilled in the art.

The 4a exon encoded polypeptide, α7-2 variant subunit polypeptide, or α7-2 variant nAChR polypeptide can be recovered and purified from genetically modified host cell cultures expressing the same by known methods including ammonium sulfate or ethanol precipitation, acid extraction, anion or cation exchange chromatography, phosphocellulose chromatography, hydrophobic interaction chromatography, hydroxyapatite chromatography or lectin chromatography. Protein refolding steps can be used, as necessary, in completing configuration of the protein. Finally, high performance liquid chromatography (HPLC) can be employed for final purification steps.

The 4a exon encoded polypeptide, α7-2 variant subunit polypeptide, or α7-2 variant nAChR polypeptide, or functional fragments or homologues thereof, of the present invention, also may be synthesized by conventional techniques known in the art, for example, by chemical synthesis such as solid phase peptide synthesis. In general, these methods employ either solid or solution phase synthesis methods (See, e.g., J. M. Stewart and J. D. Young, Solid Phase Peptide Synthesis, 2nd Ed., Pierce Chemical Co., Rockford, Ill. (1984) and G. Barany and R. B. Merrifield, The Peptides: Analysis, Synthesis, Biology, editors E. Gross and J. Meienhofer, Vol. 2, Academic Press, New York, (1980), pp. 3-254, for solid phase peptide synthesis techniques; and M. Bodansky, Principles of Peptide Synthesis, Springer-Verlag, Berlin (1984) and E. Gross and J. Meienhofer, Eds., The Peptides: Analysis, Synthesis, Biology, supra, Vol. 1, for classical solution synthesis).

In one preferred system, either the DNA or the RNA derived therefrom, both of which encode the desired 4a exon encoded polypeptide, α7-2 variant subunit polypeptide, or α7-2 variant nAChR polypeptide, may be expressed by direct injection into a cell, such as a *Xenopus laevis* oocyte. Using this method, the functionality of the polypeptide encoded by the DNA or the mRNA can be evaluated as follows (see Dascal *CRC Crit. Rev. Biochem.* 22:317-387, 1987). A variant-encoding polynucleotide is injected into an oocyte for translation into a functional receptor subunit. The function of the expressed variant α7-2 variant nAChR polypeptide can be assessed in the oocyte by a variety of electrophysiological techniques including intracellular voltage recording, two-electrode voltage clamp, patch clamp methods, and the like. The cation-conducting channel intrinsic to the nAChR opens in response to ACh or other nicotinic cholinergic agonists, permitting the flow of transmembrane current. This current can be monitored directly by voltage clamp techniques or indirectly by intracellular voltage recording, wherein changes in membrane potential due to the induced current are measured. Alternatives can include measurement of ion flux or fluorescent probes sensitive to transmembrane potential or changes in ion activity.

Receptors expressed in a genetically modified host cell may be used to identify compounds that modulate nAChR activity. In this regard, the specificity of the binding of a compound showing affinity for the receptor is demonstrated by measuring the affinity of the compound for cells expressing the receptor or membranes from these cells. This may be done by measuring specific binding of labeled (e.g., radioactive) compound to the cells, cell membranes or isolated receptor, or by measuring the ability of the compound to displace the specific binding of a standard labeled ligand. Expression of variant receptors and screening for compounds that bind to, or inhibit the binding of labeled ligand to these cells or membranes provides a method for rapid selection of compounds with high affinity for the receptor. These compounds may be agonists, antagonists or modulators of the receptor.

Expressed receptors also may be used to screen for compounds that modulate nicotinic acetylcholine receptor activity. One method for identifying compounds that modulate nAChR activity, comprises providing a cell that expresses a polynucleotide encoding a α7-2 variant nAChR polypeptide of the present invention, combining a test compound with the cell and measuring the effect of the test compound on the variant receptor activity. The cell may be a bacterial cell, a mammalian cell, a yeast cell, an amphibian cell or any other cell expressing the receptor. Preferably, the cell is a mammalian cell or an amphibian cell. Thus, for example, a test compound is evaluated for its ability to elicit an appropriate response, e.g., the stimulation of transmembrane current flow, for its ability to inhibit the response to a cholinergic agonist, or for its ability to modulate the response to an agonist or antagonist.

In addition, expressed receptors may be used to screen compounds that exhibit a cytoprotective effect. Abnormal activation of membrane channels is a potential cause of neurological disorders, such as neurodegenerative diseases (See, for example, Salamone, F. et al., *MJM*, 2000, 5:90-97; Cooper, E. C. and Jan, L. Y. *Proc. Natl. Acad. Sci. USA*, 1999, 96:4759-4766; Sharples, C. and Wonnacott, S. *Neuronal Nicotinic Receptors*, October 2001, 19:1-12; Mihailescu, S. and Drucker-Colin, R. *Arch. Med. Res.*, 2000, 31:131-144; Papke, R. L. et al., *Euro. J. Pharm.*, 2000, 393:179-195; Newhouse, P. A. and Kelton, M. *Pharm. Acta Helv.*, 2000, 74:91-101; Newhouse, P. A. et al., *Clin. Pharm.*, 1997, 11:206-228; Lloyd, G. K. and Williams, M. *J. Pharm. Exp. Therapies*, 2000, 292:461-467; Hollady, M. W. et al., *J. Med. Chem.*, 1997, 40:4169-4194; Benowitz, N. L. *Annu. Rev. Pharm. Toxicol.*, 1996, 36:597-613; Freedman, R. et al., *Harvard Rev. Psych.*, 1994, 2:179-192; and Freedman, R. et al., *J. Chem. Neuroanatomy*, 2000, 20:299-306). Examples of such neurological disorders include, but are not limited to, presenile dementia (early onset Alzheimer's disease), senile dementia (dementia of the Alzheimer's type), Parkinsonism including Parkinson's disease, Huntington's chorea, tardive dyskinesia, hyperkinesias, mania, attention deficit disorder, attention deficit hyperactivity disorder, sleep-wake disorder, chronic-fatigue syndrome, tremor, epilepsy, Tourette syndrome or other tic disorders neuropathic pain, addiction (e.g. nicotine/smoking addiction), anxiety, dyslexia, schizophrenia, and obsessive-compulsive disorder.

The α7-2 variant subunit of the present invention can be used to screen for agents useful in treating disorders such as alterations in sensory gating, immunofunction and neuropathic pain (e.g., pain associated with cancerous conditions, post herpetic neuralgia, diabetic neuropathy and osteoarthritis), as well as the foregoing list of neurological disorders.

Accordingly, nicotinic drugs are considered potential therapeutic agents in several neurological disorders, including the foregoing list of neurological disorders. Activation of the wild-type α7 nAChR appears to elicit cytoprotective properties (e.g., reduced cell lysis, see Donnelly-Roberts et al. *Brain Res.*, 1996, 719:36-44. However, it is not yet conclusively established whether a full agonist or partial agonist is preferable, nor, if the latter, what type of partial agonist is best (e.g., one that stabilizes the open and desensitized states or one that stabilizes the open and resting states of the receptor). The α7-2 variant nAChR can be used to evaluate these questions, and to select among ligands for specific types of partial agonists or specific types of antagonists.

Thus, α7 nAChR ligand pharmacology can be studied through the use of the α7-2 variant nAChR subunit of the present invention. The ability of a ligand to stabilize the desensitized state of the receptor could be evaluated by comparing the ligand's potency and efficacy at the α7-2 variant nAChR to its potency and efficacy at the wild-type α7-1 nAChR. Alternatively, the ligand's interaction with the α7-2 variant nAChR can be compared to other variants of the wild-type α7-1 nAChR. The interaction of agents with variants and the wild-type nAChR can be identified using several methods, including, but not limited to, electrophysiologic measurement of transmembrane current flow or electrical potential, measurement of the fluorescence of potential-sensitive or ion-sensitive dyes, or measurement of radioactive ion flux and a variety of α7 nAChR expression systems, for example transfected mammalian cells in culture or injected amphibian cells.

In addition to screening test agents, the expressed α7-2 variant nAChR subunit may be used to investigate mechanisms of cytotoxicity and cytoprotection. The evidence that activation of α7 nAChR is cytoprotective comes from the finding that nAChR agonists elicit cytoprotection in cells expressing the wild-type α7 nAChR subunit and that this cytoprotection is inhibited by selective α7 antagonists (for example, see Donnelly-Roberts et al. *Brain Res.*, 1996, 719: 36-44).

Cytoprotective or cytotoxic compounds that interact with the α7-2 variant nAChR of the present invention may be identified using several methods. One such method comprises providing a cell that expresses a α7-2 variant nAChR subunit of the present invention, combining a test agent with the cell, and monitoring the cell for an indicator of cytotoxicity. If it is necessary to control spontaneous action of the variant nAChR subunit, it may be stably expressed in a recombinant mammalian cell line under the control of an inducible promoter, e.g., the LacSwitch system which is inducible by isopropylthiogalactoside ("IPTG"). Expression of the α7-2 variant nAChR subunit would be maintained at a low level until induction by the addition of IPTG. Alternatively, with or without an inducible promoter, the transfected cells could be cultured in the presence of an α7 blocker, such as methyllycaconitine ("MLA") or mecamylamine, that would prevent or reduce cytotoxic action. Both blockers are reversible, permitting one to measure the effect of the test agent on α7 nAChR function after the blocker is removed (e.g., washed out).

Cytoprotective agents can be identified by their ability to reduce cell death while cytotoxic agents can be identified by their ability to promote cell death. That these effects are mediated by the α7 subunit, α7-2 variant or wild-type, can be identified by the ability of an α7 blocker to prevent the effect. Cell death, or cytotoxicity, can be monitored by a variety of techniques including but not limited to measurement of cell number or density in the culture, of cell growth rate (e.g., incorporation of labeled nucleotide or amino acid), or of cell integrity for example by uptake of a dye (e.g., trypan blue is excluded by healthy cells, or by inclusion of MTT by healthy cells), or by the release of a cytoplasmic constituent such as lactate dehydrogenase (LDH). Cytoprotective agents may also be screened for their ability to antagonize a variant nAChR to a greater extent than a wild-type nAChR, or for their ability to augment the decay rate of variant nAChR compared to the wild-type nAChR.

The present invention also includes isolated polynucleotides (e.g., detection probes or primers) capable of selectively hybridizing to a nucleic acid sequence encoding a 4a exon or an α7-2 splice variant subunit. For example, the isolated polynucleotide can be capable of selectively hybridizing to a nucleic acid sequence comprising SEQ ID NO:5 or SEQ ID NO:14, or a functional fragment or homologue of either of the foregoing. Such a detection probe will comprise a contiguous/consecutive span of at least 8, 9, 10, 11, 12, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 nucleotides. Labeled probes or primers are labeled with a radioactive compound or with another type of label as set forth above (e.g., 1) radioactive labels, 2) enzyme labels, 3) chemiluminescent labels, 4) fluorescent labels, or 5) magnetic labels). Alternatively, non-labeled nucleotide sequences may be used directly as probes or primers; however, the sequences are generally labeled with a radioactive element ($^{32}P$, $^{35}S$, $^{3}H$, $^{125}I$) or with a molecule such as biotin, acetylaminofluorene, digoxigenin, 5-bromo-deoxyuridine, or fluorescein to provide probes that can be used in numerous applications. Preferably, the isolated polynucleotide specifically hybridizes with at least 8, 9, 10, 11, 12, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 nucleotides of the nucleotide sequence encoding the α7-2 splice variant subunit. More preferably, the isolated polynucleotide specifically hybridizes with at least 4, 5, 6, 7, 8, 9, 10, 11, 12, 15, 16, 17, 18, 19, 20, 21, 22, 23, 24, 25, 26, 27, 28, 29, 30, 35, 40, 45, 50, 55, 60, 65, 70, or 75 nucleotides of the 4a exon, such as the rat or mouse 4a exon (SEQ ID NO:5 or SEQ ID NO:14, respectively), or a functionally active fragment or homologue of either of the foregoing. Optionally, the isolated polynucleotide can specifically hybridize with nucleotides within the 4a exon and outside the 4a exon. Optionally, hybridization outside the 4a exon can include hybridization to non-coding nucleotides. Such polynucleotides can be produced by recombinant or synthetic techniques.

Various degrees of stringency of hybridization can be employed. The more severe the conditions, the greater the complementarity that is required for duplex formation. Severity of conditions can be controlled by temperature, probe concentration, probe length, ionic strength, time, and the like. Preferably, hybridization is conducted under low, intermediate, or high stringency conditions by techniques well known in the art, as described, for example, in Keller, G. H., M. M. Manak, 1987, *DNA Probes*, Stockton Press, New York, N.Y., pp. 169-170.

For example, hybridization of immobilized DNA on Southern blots with $^{32}P$-labeled gene-specific probes can be performed by standard methods (Maniatis et al. [1982] *Molecular Cloning: A Laboratory Manual*, Cold Spring Harbor Laboratory, New York). In general, hybridization and subsequent washes can be carried out under intermediate to high stringency conditions that allow for detection of target sequences with homology to the exemplified polynucleotide sequence. For double-stranded DNA gene probes, hybridization can be carried out overnight at 20-25° C. below the melting temperature ($T_m$) of the DNA hybrid in 6×SSPE, 5× Denhardt's solution, 0.1% SDS, 0.1 mg/ml denatured DNA. The melting temperature is described by the following formula (Beltz et al. [1983] *Methods of Enzymology*, R. Wu, L. Grossman and K. Moldave [eds.] Academic Press, New York 100:266-285).

$Tm=81.5° C.+16.6 Log[Na^+]+0.41(\% G+C)-0.61 (\% formamide)-600/length of duplex in base pairs.

Washes are typically carried out as follows:

(1) twice at room temperature for 15 minutes in 1×SSPE, 0.1% SDS (low stringency wash);

(2) once at $T_m$−20° C. for 15 minutes in 0.2×SSPE, 0.1% SDS (intermediate stringency wash).

For oligonucleotide probes, hybridization can be carried out overnight at 10-20° C. below the melting temperature ($T_m$) of the hybrid in 6×SSPE, 5× Denhardt's solution, 0.1% SDS, 0.1 mg/ml denatured DNA. $T_m$ for oligonucleotide probes can be determined by the following formula:

$T_m$(° C.)=2(number T/A base pairs)+4(number G/C base pairs) (Suggs et al. [1981] *ICN-UCLA Symp. Dev. Biol. Using Purified Genes*, D. D. Brown [ed.], Academic Press, New York, 23:683-693).

Washes can be carried out as follows:

(1) twice at room temperature for 15 minutes 1×SSPE, 0.1% SDS (low stringency wash);

2) once at the hybridization temperature for 15 minutes in 1×SSPE, 0.1% SDS (intermediate stringency wash).

In general, salt and/or temperature can be altered to change stringency. With a labeled DNA fragment>70 or so bases in length, the following conditions can be used:

Low: 1 or 2×SSPE, room temperature

Low: 1 or 2×SSPE, 42° C.

Intermediate: 0.2× or 1×SSPE, 65° C.

High: 0.1×SSPE, 65° C.

By way of another non-limiting example, procedures using conditions of high stringency can also be performed as follows: Pre-hybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65° C., the preferred hybridization temperature, in pre-hybridization mixture containing 100 μg/ml denatured salmon sperm DNA and 5-20×$10^6$ cpm of $^{32}P$-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art and as cited in Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y. are incorporated herein in their entirety.

Another non-limiting example of procedures using conditions of intermediate stringency are as follows: Filters containing DNA are pre-hybridized, and then hybridized at a temperature of 60° C. in the presence of a 5×SSC buffer and labeled probe. Subsequently, filters washes are performed in a solution containing 2×SSC at 50° C. and the hybridized probes are detectable by autoradiography. Other conditions of intermediate stringency which may be used are well known in the art and as cited in Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y. are incorporated herein in their entirety.

Duplex formation and stability depend on substantial complementarity between the two strands of a hybrid and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions and deletions can be produced in a given polynucleotide sequence in many ways, and these methods are known to an ordinarily skilled artisan. Other methods may become known in the future.

A "complementary" polynucleotide sequence, as used herein, generally refers to a sequence arising from the hydrogen bonding between a particular purine and a particular pyrimidine in double-stranded nucleic acid molecules (DNA-DNA, DNA-RNA, or RNA-RNA). The major specific pairings are guanine with cytosine and adenine with thymine or uracil. A "complementary" polynucleotide sequence may also be referred to as an "antisense" polynucleotide sequence or an "antisense sequence".

The present invention also includes pharmaceutical compounds useful for treating conditions associated with neurodegenerative processes, enzymatic function, affective disorders or immuno function, comprising an agent that regulates the function of a variant of the wild-type nAChR α7 subunit comprising the amino acid sequence selected from the group consisting of SEQ ID NO:1 and SEQ ID NO:15, or a functional fragment or homologue of either of the foregoing; and a pharmaceutically acceptable carrier.

The pharmaceutical compounds of the subject invention can be formulated according to known methods for preparing pharmaceutically useful compositions. Formulations are described in a number of sources which are well known and readily available to those skilled in the art. For example, *Remington's Pharmaceutical Sciences* (Martin E W [1995] Easton, Pa., Mack Publishing Company, 19$^{th}$ ed.) describes formulations which can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

The present invention also includes antibodies (e.g., monoclonal or polyclonal) and antibody fragments that specifically bind to a variant nAChR α7-2 subunit comprising the amino acid sequence selected from the group consisting of SEQ ID NO:1 and SEQ ID NO:15, or a functional fragment or homologue of either of the foregoing. Antibodies that are immunospecific for the polypeptides as set forth herein are specifically contemplated. In various embodiments, antibodies that do not cross-react with other proteins (such as *A. marginale* MSP5) are also specifically contemplated. The antibodies of the subject invention can be prepared using standard materials and methods known in the art (see, for example, *Monoclonal Antibodies: Principles and Practice*, 1983; *Monoclonal Hybridoma Antibodies: Techniques and Applications*, 1982; *Selected Methods in Cellular Immunology*, 1980; *Immunological Methods, Vol. II*, 1981; *Practical Immunology*, and Kohler et al. [1975] *Nature* 256:495). These antibodies can further comprise one or more additional components, such as a solid support, a carrier or pharmaceutically acceptable excipient, or a label.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity, particularly neutralizing activity. "Antibody fragments" comprise a portion of a full-length antibody, generally the antigen binding or variable region thereof. Examples of antibody fragments include Fab, Fab', F(ab')$_2$, and Fv fragments; diabodies; linear antibodies; single-chain antibody molecules; and multi-specific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. [1975] *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. [1991] *Nature* 352: 624-628 and Marks et al. [1991] *J. Mol. Biol.* 222: 581-597, for example.

The monoclonal antibodies described herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. [1984] *Proc. Natl. Acad. Sci. USA* 81: 6851-6855). Also included are humanized antibodies, such as those taught in U.S. Pat. Nos. 6,407,213 or 6,417,337 which are hereby incorporated by reference in their entirety.

Single-chain Fv" or "sFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in The Pharmacology of Monoclonal Antibodies [1994] Vol. 113:269-315, Rosenburg and Moore eds. Springer-Verlag, New York.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The terms "comprising", "consisting of" and "consisting essentially of" are defined according to their standard meaning. The terms may be substituted for one another throughout the instant application in order to attach the specific meaning associated with each term. The phrases "isolated" or "biologically pure" refer to material that is substantially or essentially free from components which normally accompany the material as it is found in its native state. Thus, isolated peptides in accordance with the invention preferably do not contain materials normally associated with the peptides in their in situ environment. "Link" or "join" refers to any method known in the art for functionally connecting peptides, including, without limitation, recombinant fusion, covalent bonding, disulfide bonding, ionic bonding, hydrogen bonding, and electrostatic bonding.

The practice of the present invention can employ, unless otherwise indicated, conventional techniques of molecular biology, microbiology, recombinant DNA technology, electrophysiology, and pharmacology, that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover ed. 1985); Perbal, B., A Practical Guide to Molecular Cloning (1984); the series, Methods In Enzymology (S. Colowick and N. Kaplan eds., Academic Press, Inc.); Transcription and Translation (Hames et al. eds. 1984); Gene Transfer Vectors For Mammalian Cells (J. H. Miller et al. eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. eds. (1991) IRL Press)).

Materials and Methods

RT-PCR Method. The expression of α7 nicotinic receptor subunit splice variants in central and peripheral neurons was examined using RT-PCR techniques similar to those previously reported. Total RNA was isolated from intracardiac ganglia and associated tissue, superior cervical ganglia (SCG) and brain. RNA was reverse-transcribed and cDNA amplified using SUPERSCRIPT One-Step RT-PCR with PLATINUM TAQ (INVITROGEN Co., San Diego, Calif., USA). As a negative control, an RT-PCR reaction with only water was conducted to eliminate the possibility of false positives due to contaminating α7 cDNAs. Primers specific for the cc7 gene product (α7-P1) were designed to span an intron in order to discriminate between genomic DNA and cDNA. Table 2 lists the sequences of the primers used in this study and the predicted size for the products.

For single cell RT-PCR experiments, intracardiac neurons were dissociated from 4-7 day-old neonatal rats, and cytoplasm extracted from isolated neurons as previously described (Zhang and Cuevas, J. Neurophysiol., 2002, June; 87(6):2867-79). All procedures were done in accordance with the regulations of the Institutional Animal Care and Use Committee. Briefly, the cellular content of individual neurons was harvested using the dialyzing whole-cell configuration of the patch-clamp technique. The patch pipettes were filled with 3 µl of 1× SUPERSCRIPT One-Step RT-PCR Reaction Mix (INVITROGEN Co.) containing 1 U/µl RNAsin (PROMEGA Co. Madison, Wis., USA). Following extraction of the cytoplasm, the content of the pipette was expelled into a microfuge tube and quickly frozen on dry ice. Single cell RT-PCR experiments were conducted immediately following the extraction using SUPERSCRIPT One-Step RT-PCR with Platinum Taq (INVITROGEN Co.). Negative controls for these experiments involved suctioning extracellular solution via a patch pipette located directly above the cells. These controls were carried through all subsequent reactions to rule out the possibility of contamination from cytoplasm from nearby cells or other clones isolated in the laboratory. PCR products were gel purified using a QIAEX II Gel Purification kit (QIAGEN) and sequenced by the Molecular Biology Core Facility at the H. Lee Moffitt Cancer Center and Research Institute.

Genomic DNA Extraction and PCR Amplification Method Genomic DNA was isolated from the livers of 7 day-old neonatal rats using the WIZARD Genomic DNA Purification Kit (PROMEGA). Rats were killed by decapitation for these experiments. Primer pairs were designed to detect the presence of introns flanking the putative exon 4a of the rat α7 gene. One primer pair, α7-P2, consisted of a sense primer located in exon 4 and an antisense primer that was specific to the insert of the α7-2 variant. A second primer pair, α7-P3, consisted of a sense primer specific for the α7-2 insert and an antisense primer specific for exon 5. Genomic DNA was amplified by PCR in 50 µl reactions containing 1×PCR buffer, 2.0 mM $MgCl_2$, 0.2 mM each dNTP, 0.2 µM each primer, and 1.25 units HOTSTARTAQ polymerase (QIAGEN). A negative control that lacked template DNA was also included. Reactions were initiated with a 15 minute 95° C. denaturation followed by 40 cycles of 95° C. for 30 seconds, 58° C. for 45 seconds and 72° C. for 3 minutes. The cycles were followed by a final extension period of 7 minutes at 72° C. PCR products were electrophoresed through a 1% TBE agarose gel, stained with ethidium bromide and visualized through UV illumination.

Immunoblot Analysis. Whole brains and superior cervical ganglia (SCG) were dissected from 10-14 day-old neonatal rats, and intracardiac ganglia (ICG) from postnatal day 1-5 rats. For brain and intracardiac ganglia dissections animals were killed by decapitation, and by $CO_2$ asphyxiation for SCG dissections. Tissues were homogenized in a 2% Triton X-100 extraction buffer containing 50 mM sodium phosphate, pH 7.4 and the following protease inhibitors: iodoacetamide (0.4 mM), benzamidine (5 mM), phosphoramidon (5 µg/ml), soybean trypsin inhibitor (10 µg/ml), leupeptin (10 µg/ml), pepstatin A (20 µg/ml), EDTA (5 mM), EGTA (5 mM), aprotinin (2 µg/ml), and phenylmethylsulfonyl fluoride (1 mM). Homogenates were sedimented at 15,000 rpm for 15 minutes at 4° C. and the supernatant centrifuged at 33,000 rpm for one hour at 4° C. The supernatant containing the detergent extracts was collected and stored at −20° C. prior to experiments.

Protein concentrations of the detergent extracts were determined using the BIORAD Protein Assay I (BIORAD, Hercules, Calif.). For immunodepletion, AChRs were immunotethered to microtiter wells in a manner described previously for solid-phase immunoprecipitations (Conroy and Berg, *J. Biol. Chem.*, 1995, March, 270(9):4424-4431; Cuevas et al., *J. Physiol.*, 2000, 525: 735-746). Equal amounts of extract were incubated overnight with constant agitation at 4° C. in wells containing a 1:1000 dilution of the α7 subunit-specific mAb 319 (SIGMA RBI, Natick, Mass.) anchored with rabbit-anti-rat IgG (depleted) or in wells containing only rabbit-anti-rat IgG (mock-depleted control). In some experiments, donkey-anti-rabbit was used as the anchoring antibody. As a negative control, solubilization buffer (with no protein) was incubated in the antibody-coated microtiter wells and tested for immunoreactivity. No bands were detected in immunoblots of these blank experiments. All protein extracts were solubilized in sample buffer (0.125 M Tris-HCl, pH 8.8, 4% SDS, 20% glycerol, 10% beta-mercaptoethanol; TBS), heated to 95° C. for five minutes, electrophoresed at 100 volts through a 10% precast polyacrylamide gel (BioRad) and electroblotted to PVDF (IMMOBILON P; MILLIPORE) at 100 volts for two hours. The anti-α7-2 polyclonal antibody, Ab 87, was generated in rabbits against a fusion peptide with sequence identical to the deduced amino acid sequence of exon 4a (FABGENNIX, Inc., Shreveport, La.). Blots were blocked with 5% nonfat dried milk in TBS containing 0.5% Tween 20 (TBST) for two hours and incubated for two hours with the primary polyclonal antibody Ab 87 diluted 1:50 in a 2.5% nonfat dried milk/TBST solution. Following three TBST washes, blots were incubated for an hour with a goat-anti-rabbit secondary antibody conjugated to horseradish peroxidase (SANTA CRUZ BIOTECHNOLOGY, Inc., Santa Cruz, Calif.) diluted 1:10,000 in TBST. Membranes were washed four times with TBST and signals were detected with chemiluminescent visualization (ECL; Santa Cruz, Calif.).

Oocyte Recordings. Intrinsic cardiac neuron RNA extracts were amplified by RT-PCR using the primers α7-P1, and the resulting α7-2 cDNA gel purified (QIAGEN Gel Extraction Kit). The full-length α7-2 subunit was then generated by splicing the α7-2 cDNA into a rat α7-1 clone using the restriction enzymes Cfr 101 and Eco47 III (ROCHE DIAGNOSTICS Co.). The full-length α7-2 cDNA was inserted into the multicloning site of the pcDNA 3.1 plasmid using the enzymes Hind III and Xho I (ROCHE DIAGNOSTICS Co.). Both α7-1 and α7-2 subunit cDNAs (in pcDNA 3.1) were linearized with the restriction enzyme Pvu II, which preserves a several-hundred-base pair tail to increase cRNA stability in the oocyte, transcribed using MEGASCRIPT Kit (AMBION, Austin Tex.) and $m^7G(5')ppp(5')G$-capped. Integrity and yield of the cRNA was verified on a 1% formaldehyde agarose gel.

*Xenopus laevis* (Xenopus I, Ann Arbor, Mich.) were anesthetized using tricaine methane sulfonate, and oocytes surgically removed from the frog and placed in a solution that consisted of 82.5 mM NaCl, 2.5 mM KCl, 10 mM HEPES, 2 mM $CaCl_2$, 1 mM $MgCl_2$, 10 mM $Na_2HPO_4$, 50 units/ml penicillin, and 50 μg/ml streptomycin, pH 7.5. Oocytes were dispersed in this same solution minus $Ca^{2+}$ and plus 0.3% Collagenase A (ROCHE DIAGNOSTICS Co., Indianapolis Ind.). After isolation, the oocytes were thoroughly rinsed, and stage VI oocytes were separated and maintained overnight at 18°. Micropipettes for injection of cRNA were pulled on a Sutter P87 horizontal puller. The α7-2 cRNA was diluted in diethylpyrocarbonate-treated water, and drawn up into the micropipette with negative pressure. Approximately 10-50 ng of α7-2 cRNA was injected into the oocytes by applying positive pressure using a PICOSPRITZER II (GENERAL VALVE CORPORATION, Fairfield, N.J.).

Recordings were conducted 3-4 days following injection. Oocytes were placed in a small volume chamber (<100 μl) and continuously perfused via a 1.5 mm glass pipette positioned ~1 mm from the oocyte. The glass pipette was connected to a low volume MP-8 perfusion manifold (Warner), permitting rapid solution change (<1 s). Solutions were applied via gravity feed regulated by solenoid valves (PARKER-HANNIFIN, Cleveland, Ohio) controlled by a valve driver (PARKER-HANNIFIN) and a Master 8 TTL pulse generator (A.M.P.I., Jerusalem, Israel). Recording microelectrodes with final resistance of 1-3 μΩ were fabricated with NARISHIGE PP-83 puller (NARISHIGE, East Meadow, N.Y.) and filled with 3 M KCl. Standard two-electrode voltage-clamp techniques were used to record currents in response to agonist application. Data were amplified using a TURBO TEC-05 amplifier (ALA Scientific Instruments Inc., Westbury, N.Y.), digitized at 1 kHz with a VR-10B digitizer (INSTRUTECH Co., Port Washington, N.Y.) and recorded on a computer with the PULSE 8.5 program (HEKA Electronics Co., Lambrecht, Germany).

The control external solution for voltage clamp recordings consisted of (in mM): 115 NaCl, 2.5 KCl, 1.8 $CaCl_2$, and 10 HEPES (pH 7.2). The recording chamber was continuously perfused (10 ml/min), and drugs applied using the application system described above.

EXAMPLE 1

Rat Intracardiac Neurons Express Splice Variants of the α7 Gene

To test the hypothesis that rat intracardiac neurons express splice variants of the α7 gene product, intrinsic cardiac neurons were studied using RT-PCR techniques. Oligonucleotide primers α7-P1; see Table 2) were designed to amplify a 653 bp region corresponding to nucleotide positions 109 to 761 of the *Rattus norvegicus* nicotinic acetylcholine receptor α7 subunit mRNA (GI: 3478618). This region is known to encode the extracellular domain containing both the α-bungarotoxin and competitive agonist binding sites. Table 2 lists the sequence of oligonucleotide primers used in this study and the predicted size for the individual products. FWD, forward (sense); REV, reverse (antisense). Primers specific for the splice insert are shown in bold italics.

TABLE 2

| Name | Sequence | | Product Size (bp) and Specificity |
|---|---|---|---|
| α7-P1 | FWD GTACAAGGAGCTGGTCAAGAACTACAACC | (SEQ ID NO:6) | 653 (α7-1) |
| | REV GGGCTGAAATGAGTACACAAGG | (SEQ ID NO:7) | 740 (α7-2) |
| α7-P2 | FWD GGAGTGAAGAATGTTCGTTTTCCAG | (SEQ ID NO:8) | 91 (α7-2) |
| | REV _CTTGGTTCAAAATGCAACTGACACC_ | (SEQ ID NO:9) | |

TABLE 2-continued

| Name | Sequence | Product Size (bp) and Specificity |
|---|---|---|
| α7-P3 | FWD AGTTGCATTTTGACCAAGATCTGC (SEQ ID NO:10)<br>REV CAAAACATTGGTGTGGAACGTG (SEQ ID NO:11) | 122 (α7-2) |
| α7-P4 | FWD GGTGTCAGTTGCATTTTGACCAAG (SEQ ID NO:12)<br>REV GGGCTGAAATGAGTACACAAGG (SEQ ID NO:13) | 474 (α7-2) |

FIG. 1A shows results of a representative RT-PCR experiment using primers α7-P1 to amplify RNA isolated from intracardiac neurons and associated tissues. Several products with sizes ranging from 400-750 bp were readily detectable in all of our reactions (FIG. 1A, n>10). Cloning and sequencing of the products indicated that several of these products represented splice variants of the α7 gene.

The conventional or wild-type α7 gene product (α7-1; FIG. 1A) is composed of 10 exons, with the first transmembrane domain encoded in exon 7 (FIG. 1B). Three of the α7 splice variants previously identified in intrinsic cardiac neurons are the result of deletions of all or parts of exons 3-6 (FIG. 1C). All of these splice variants result in a frame shift, and contain a premature stop codon prior to the region encoding the competitive agonist-binding site. In contrast, the splice variant of the present invention (α7-2; FIG. 1A) contains an 87 bp insert between the regions encoded by exons 4 and 5 (FIG. 1C). FIG. 2 shows the sequence of the insert contributing to α7-2, and flanking regions, aligned to the conventional α7 gene product. The insert preserves the reading frame of the transcripts, and the deduced amino acid sequence is provided in FIG. 2. The predicted protein sequence for the insert was analyzed using multiple algorithms on the Network Protein Sequence Analysis Server (Lyon, France). Results suggest that the secondary structure of the domain encoded by the α7-2 insert is an alpha helix flanked by random coils.

EXAMPLE 2

Identification of a Novel Exon in the α7 Gene

To determine if the 87 bp insert represents a shift in the donor or acceptor sites of exon 4 and/or exon 5, respectively, rat genomic DNA was probed using primers specific for the insert and flanking sequences. FIG. 3 shows the results obtained using the α7-P2 and α7-P3 primer pairs (see Table 2). Primer pair α7-2 has a forward primer specific for exon 4 and a reverse primer specific for the α7-2 insert, whereas primer pair α7-P3 has a forward primer specific for the insert and a reverse primer specific for exon 5. A 505 bp product was detected that included exon 4 and the α7-2 insert at the 5' and 3' ends, respectively. A sequence of the product, aligned to the α7-2 splice variant, is shown in FIG. 4, and indicates the presence of a putative 459 bp intron between exon 4 and the α7-2 insert. Consistent with an intron, the 459 bp section contains consensus donor and acceptor sequences at the 5' and 3' ends, respectively (FIG. 4). Amplification of genomic DNA using primers α7-P3, specific for the α7-2 insert and exon 5, failed to yield any product, even though these primers could readily amplify cDNA encoding the α7-2 splice variant (FIG. 4; cDNA, α7-P3). Intron 4 in the human α7 gene is known to be >25 k bp and such a large product would not have been detected by our methods, thus explaining the lack of product in our genomic DNA PCR reaction. Taken together, these data suggest that the α7-2 splice variant is produced via the incorporation of a novel exon, exon 4a, of the α7 subunit gene.

EXAMPLE 3

The α7-2 Splice Variant is Found in Brain and in Both Sympathetic and Parasympathetic Neurons Experiments were conducted to test for the presence of α7-2 subunit mRNA in the central nervous system and in other peripheral neurons, to determine if expression of this subunit is limited to intracardiac ganglia. The expression of α7-2 in the superior cervical ganglion was of particular interest because these neurons exhibit ACh-evoked currents mediated by α7-nAChRs similar to those expressed in intrinsic cardiac neurons. To facilitate detection of the α7-2 splice variant, a set of primers (α7-P4, see Table 2) was designed with the forward primer specific for the α7-2 isoform. FIG. 5A shows the results of a representative RT-PCR experiment using primers α7-P2 on RNA extracts from neonatal rat SCG and brain. The α7-2 transcripts were detected in both the central nervous system and in superior cervical ganglia, suggesting that expression of this transcript is not a phenomenon exclusively associated with intracardiac neurons. Experiments were also conducted to determine if any other sequence variations in the α7 gene product are linked with the exon 4a cassette insert. RT-PCR analysis of intrinsic cardiac neuron RNA extracts using primers specific for the insert and regions upstream and downstream of the splice (exons 1-10) failed to detect any other sequence variations (n=20, data not shown).

EXAMPLE 4

The α7-2 Splice Variant is Found in Intracardiac Neurons

Figure 5B:
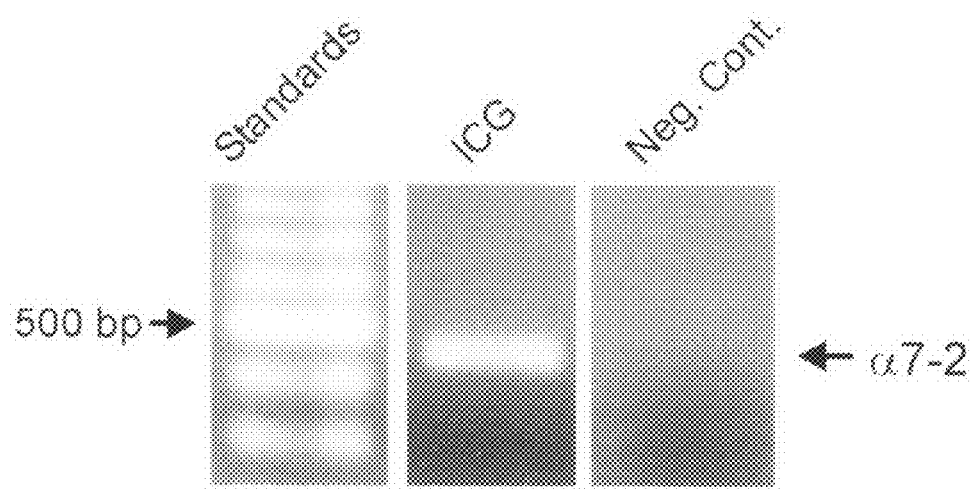

Given that α7 subunits have been detected in non-neuronal cells, it seemed prudent to test for the expression of α7-2 at the single cell level. Intrinsic cardiac neurons were isolated and probed for α7-2 expression using single cell RT-PCR techniques similar to those previously reported. FIG. 5B shows the results obtained for an intracardiac neuron using the α7-P4 primers. A product of the predicted size for the α7-2 was detected in 5 out of 7 neurons tested, which is similar to numbers reported previously in intrinsic cardiac neurons for the α7 subunit using single cell RT-PCR. Cloning and sequencing of these PCR products confirmed that they represented the α7-2 subunit.

EXAMPLE 5

Expression of the α7-2 Splice Variant is Detected in Central and Peripheral Neurons To determine if transcripts encoding the α7-2 isoform are translated in central and peripheral neurons, rat brain and intracardiac and superior cervical ganglia were examined for α7-2 subunit protein expression. Protein extracts from the respective tissues were analyzed by probing immunoblots with the α7-2-specific polyclonal antibody, Ab 87 (FIG. 6A). A band of the predicted size for the α7-2 protein (~58 kDa) may be readily detected in protein extracts from all tissues. To confirm that this band represents the α7-2 product, extracts were preincubated in microtiter wells coated with rabbit-anti-rat IgG (mock-depleted) or with rabbit-anti-rat IgG and the anti-α7 monoclonal antibody, mAb 319 (immunodepleted). The mAb 319 antibody is known to bind to the large intracellular loop between transmembrane domains 3 and 4 of the α7-1 subunit. The amino acid sequence of the α7-2 subunit peptide is expected to be identical to that of α7-1 in this region, and thus mAb 319 should immunoprecipitate both α7-1 and α7-2 containing AChRs. Immunoblot experiments were then conducted on the mock-depleted or immunodepleted extracts using the anti-α7-2 polyclonal antibody, Ab 87. A band of the size predicted for the α7-2 monomer (58 kDa) was readily detectable in immunoblots of mock-depleted extracts of all three tissues (FIG. 6B). However, the levels of this product were significantly reduced in extracts immunodepleted of α7 subunits with mAb 319 (FIG. 6B). This observation confirms the expression of α7-2 in peripheral and central tissues and verifies that Ab 87 is specific for α7-2.

EXAMPLE 6

The α7-2 Splice Variant Forms Functional Acetylcholine Receptors

Figure 7A:
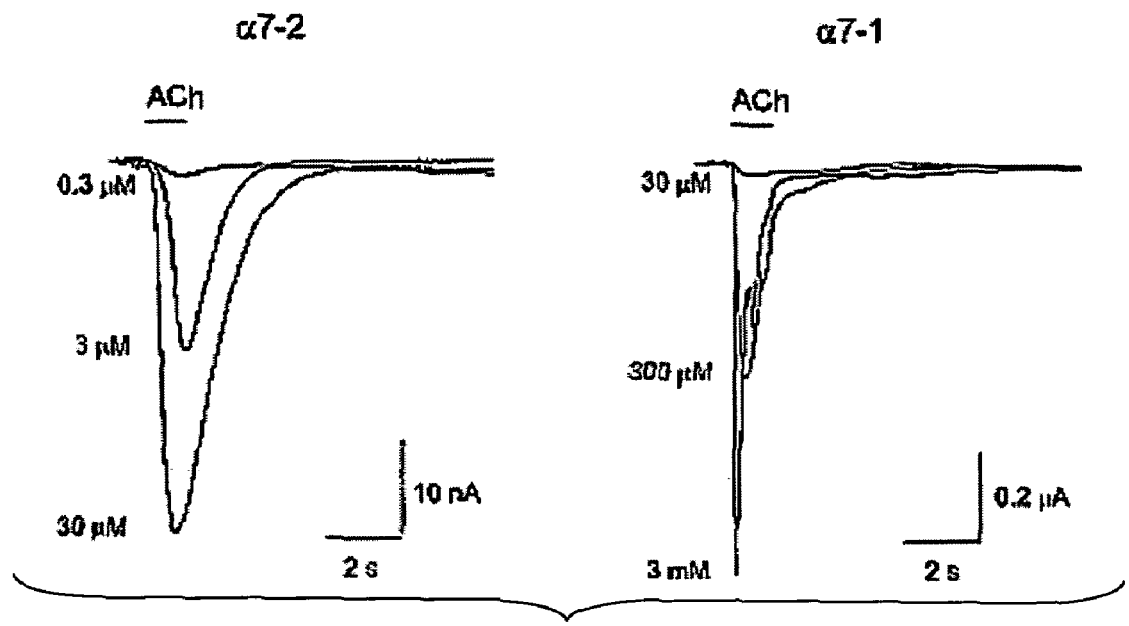
FIGS. 7A and 7B show that the α7-2 splice variant forms functional acetylcholine receptors in *Xenopus* oocytes.
Figure 7B:
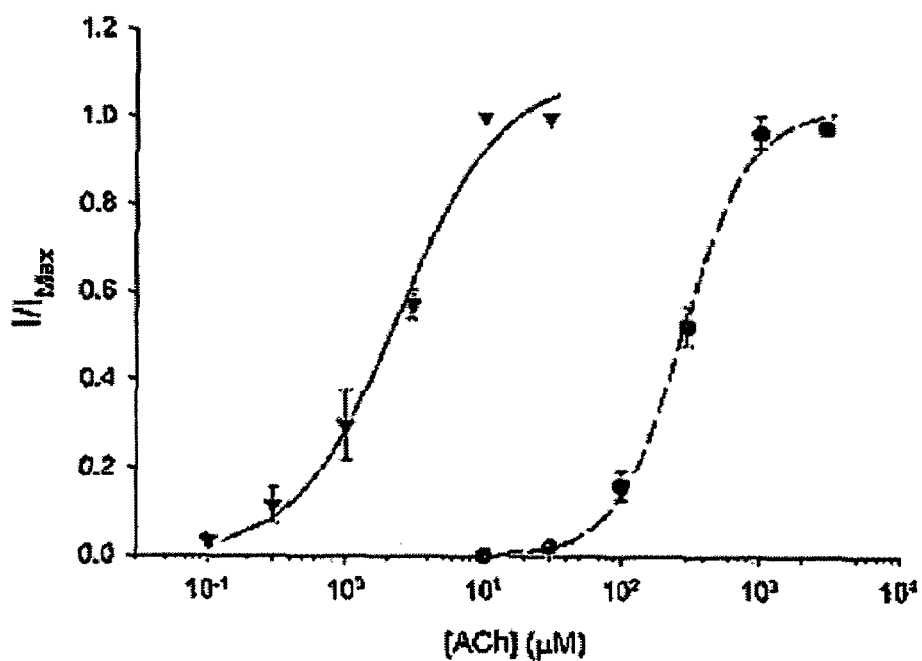

The ability of the α7-2 subunit to form functional homomeric ligand gated ion channels was examined in *Xenopus* oocytes using two-electrode voltage-clamp experiments. FIG. 7A shows a family of current traces evoked by ACh at the indicated concentrations from an oocyte injected with cRNA generated from the in vitro transcription of α7-2 (left traces) or α7-1 (right traces) DNA templates. A plot of the mean concentration-response relationship for ACh activation of α7-2 homopentamers is shown in FIG. 7B (n=5). A fit of the data using the Hill equation indicates that the α7-2-nAChRs were half maximally activated by 2.4 μM ACh and that maximal activation occurs at 10 μM ACh. In contrast, in oocytes injected with α7-1 cRNA, ACh-evoked currents were half maximally activated at 278 μM ACh, with maximal activation at 1 mM ACh (FIG. 7B, n=5). The Hill coefficients were 1.2 and 1.8 for α7-2 and α7-1, respectively. These data indicate that the α7-2 subunit is capable of forming functional AChRs in *Xenopus* oocytes. Moreover, α7-2-nAChRs are markedly more sensitive to ACh than α7-1-nAChRs.

EXAMPLE 7

α7-2 nAChRs Bind α-Bungarotoxin Reversibly

Figure 8A:
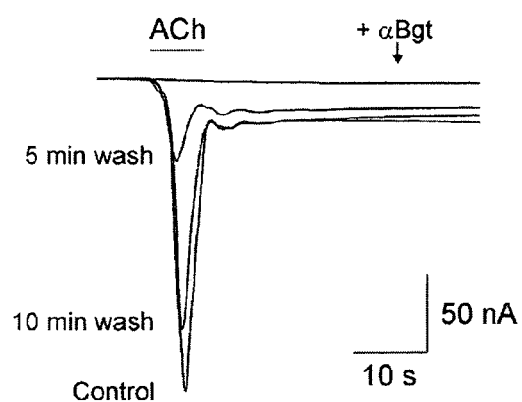
FIGS. 8A-8D demonstrate that α7-2-nAChRs bind α-bungarotoxin reversibly and desensitizes more slowly than α7-1-nAChRs.
Figure 8B:
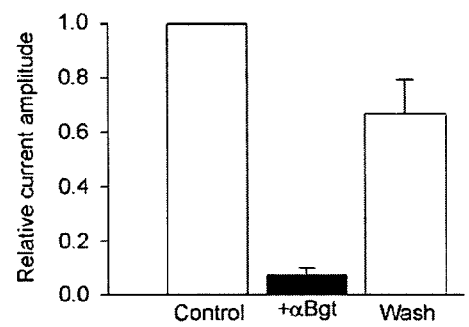

One of the distinct characteristics of α7-nAChRs is their high affinity for α-bungarotoxin. To determine if sensitivity to αBgt is preserved in α7-2-nAChR, ACh-evoked currents were recorded from oocytes injected with α7-2 cRNA in the absence and presence of toxin. FIG. 8A shows a family of transient currents evoked by application of 100 μM ACh onto a single oocyte voltage clamped at a membrane potential of −70 mV. α-Bungarotoxin (50 nM) significantly attenuated the ACh-evoked response, and in four similar experiments 50 nM αBgt inhibited the peak ACh-evoked current by 93±3% (FIG. 8B). The inhibition by toxin was rapidly reversible and following a 5 min wash the ACh-evoked current recovered to near control levels, as shown in FIG. 8B. In contrast, in oocytes injected with α7-1 cRNA, αBgt-block of ACh-evoked currents did not appreciably reverse over a similar time interval. Thus, the α7-2 subunit contributes to αBgt-sensitive nAChRs, but there is a significant difference in the αBgt binding-properties of α7-1- and α7-2-nAChRs subtypes.

EXAMPLE 8

α7-2 nAChRs Desensitize More Slowly than α7-1 nAChRs

Figure 8C:
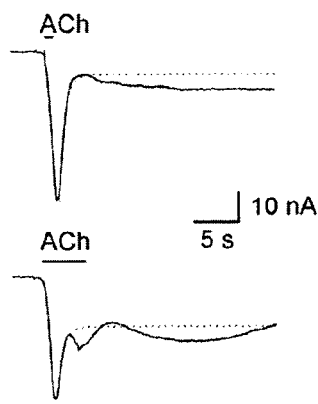
Figure 8D:
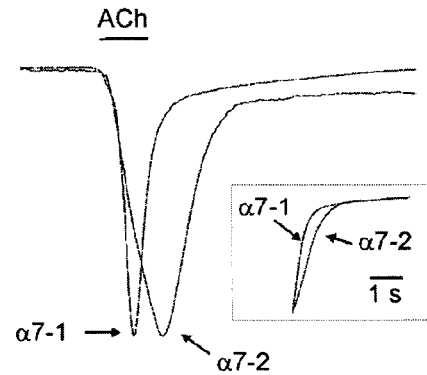

A distinguishing attribute of α7-1 containing receptors is their rapid rate of desensitization. To determine if the kinetic properties of α7-2-nAChRs resemble those of α7-1-nAChRs, the rate of whole-cell current decay of α7-2-nAChRs was recorded following 1 s and 5 s applications of 3 μM ACh (FIG. 8C). Under both conditions the whole-cell ACh-evoked current exhibited both a transient and a sustained component. Bath application of 50 nM α-bungarotoxin (αBgt) abolished both components of the current (see FIG. 8A). It has been shown in oocytes injected with α7-1 cRNA that the rapidly decaying component represents activation and desensitization of nAChRs, whereas the slower component is due to the opening of calcium-activated chloride channels (Seguela et al., *J. Neurosci.*, 1993, 13: 596-604; Peng et al., *Mol. Pharmacol.*, 1994, 45:546-554). In both 1 s and 5 s applications, the fast decaying component was best fit by a single exponential with a time constant (τ) of 1.2 s. Thus, increasing ACh application beyond 1 s does not appear to alter the rate of α7-2-nAChR decay, and this decay phase likely represents receptor desensitization. The amplitude of the slowly decaying component, representing calcium-activated chloride channels ($I_{Cl(Ca)}$), was increased by longer applications. Therefore, to minimize $I_{Cl(Ca)}$ contamination, 1 s pulses of ACh were used to compare the desensitization rates of α7-1 and α7-2 homopentamers expressed in oocytes. For these experiments, ACh was applied at the $EC_{50}$ determined here for each splice variant, since increasing the ACh concentration above the $EC_{50}$ is known to accelerate the rate of desensitization of AChRs. FIG. 8D shows superimposed representative ACh-evoked responses mediated by α7-1-nAChRs (300 μM ACh) and α7-2-nAChRs (3 μM ACh) scaled to peak α7-1-nAChRs current amplitude. ACh-evoked currents in oocytes injected with α7-2 cRNA exhibited slower activation and desensitization kinetics than those observed in oocytes injected with α7-1 cRNA. Time to peak current amplitude was 400 ms for α7-1 but 1.6 ms for α7-2 (FIG. 8D). In similar experiments time to peak was 350±65 ms for α7-1-nAChRs (n=5) but 1.35±0.13 s for α7-2-nAChRs (n=5). For both channel types, the fast decaying component of the ACh-evoked response was best fit by a single exponential. However, the rate of decay for α7-1-nAChRs was best fit with an exponential function with τ=559 ms, whereas that of α7-2-nAChRs was best fit with an exponential function with τ=1.52 s. In five similar experiments τ was 609+62 ms and 1.37±0.05 s for α7-1-nAChRs and α7-2-nAChRs, respectively.

The principal finding reported here is that multiple isoforms of the α7 gene product are generated in central and peripheral neurons. A novel α7 isoform, α7-2, was shown to form functional α-bungarotoxin sensitive homomeric receptors when expressed in *Xenopus* oocytes. The α7-2-AChRs desensitize slowly, bind αBgt in a rapidly reversible manner and have a higher affinity for ACh than α7-1-nAChRs. This isoform is produced by the incorporation of a novel cassette exon, exon 4a, near the N-terminus of the receptor. Transcripts encoding this splice variant were detected in both central and peripheral neurons. Moreover, immunoblot analysis indicated the functional expression of the α7-2 subunit in these tissues.

The observation reported here of two functional α7 splice variants may resolve some of the long standing controversy surrounding the structure and function of receptors containing the α7 nicotinic receptor subunit. Various lines of evidence suggest that the α7 subunit does not combine with other known nAChR gene products with the exception of the chick α8. Biochemical studies using subunit-specific antibodies failed to detect the presence of other non-α7 subunits assembling with the α7 gene product. Also, the conventional α7 gene product, α7-1, was shown to form functional homomeric channels when expressed in exogenous systems including *Xenopus* oocytes, SH-EP1 cells and $GH_4C_1$ cells. The pharmacological and electrophysiological properties of these channels were nearly identical to those of native α7-nAChRs studied in various cell types, such as rat hippocampal neurons, chick ciliary neurons and PC-12 cells. However, electrophysiological studies on various cell types suggested the presence of heterogenous populations of α7-nAChRs exhibiting distinct pharmacological and biophysical properties. For example, in rat superior cervical ganglion neurons, two distinct α7-nAChR types were detected. Type I α7-nAChRs in SCG neurons desensitize rapidly, are activated by choline and are blocked by αBgt in an irreversible manner; whereas Type II α7-nAChRs desensitize slowly, are insensitive to choline and bind αBgt in a rapidly reversible manner. Similarly, it has been proposed that chick sympathetic neurons express multiple α7-nAChR subtypes, with the α7-selective antagonist methyllycaconitine discriminating between the different α7-nAChR subtypes.

Experiments have also indicated that the α7 subunit contributes to all αBgt-binding receptors in the central nervous system. These studies showed that α7-null mice lacked αBgt binding sites in the CNS and fast nicotinic currents. However, the α7-knockout mouse was generated by a deletion of exons 8-10 of the α7 gene. These exons are also incorporated into the α7-2 subunit, and thus these mice would lack both α7-1- and α7-2-nAChRs. While an α7 gene product may contribute to all αBgt binding AChRs (αBgt-nAChRs) in the central nervous system, our data suggest that there are two isoforms of the α7 subunit which contribute to αBgt-nAChRs in the CNS. While the data strongly suggest that α7-1 subunits do not combine with other known AChR subunits, it remains to be determined if α7-1 and α7-2 combine to form heteropentamers or if they exist as discrete homopentameric receptors.

The hypothesis that the α7 subunit exists in multiple isoforms that contribute to α7-nAChRs subtypes was has been proposed. Such α7 receptor isoforms would permit functional diversity while being consistent with studies that suggest that the α7 subunit does not combine with other nAChR subunit species. Splice variations of ligand-gated ion channels such as the NMDA receptor, the 5-HT3 receptor, and the GABA-A receptor have been shown to contribute to functional channels and affect the pharmacological and/or biophysical properties of the channels. However, no splice variations of nicotinic acetylcholine subunits have previously been shown to contribute to AChRs with distinct characteristics. This lack of sequence variants of nicotinic receptors is surprising, given that most genes encoding AChR subunits contain between five and ten exons, and thus numerous splice possibilities exist. Reports indicate that the α4 subunit exists in two isoforms, but when these respective isoforms are incorporated into functional channels containing the β2 subunit, they are indistinguishable. The α1 subunit has also been shown to exist in multiple sequence variants, but only one of these isoforms assembles functional ACh receptors. Previous studies have identified several splice variants of the α7 in human brain; all but one of these splice variants contained a premature stop codon. In bovine chromaffin cells, a splice variant of the α7 subunit has also been detected where the exon that codes for the M2 transmembrane domain is deleted. This splice variant does not yield functional channels when expressed in *Xenopus* oocytes, but inhibits the expression of α7-1 homomers when co-injected with the full-length isoform. It remains to be determined if the α7 splice variants detected here, which contain a premature stop codon, can regulate expression of the α7-1 and α7-2 isoforms in a similar manner. None of these previously reported isoforms were detected in rat neurons in the present study.

The N-terminal location of the insert within the α7-2 subunit suggests close proximity to the ACh-binding pocket. This theory is in part supported by the crystal structure of the molluscan acetylcholine-binding protein. This protein is a homologue of the amino-terminal ligand-binding domain of the α7-1 subunit, and thus provides insight into the putative structure of this domain. From the crystalline structure, it was determined that three principal loops (A-C) and three complimentary loops (D-F) compose the α7 acetylcholine-binding site. Exon 4a is inserted between the regions that encode principal loop A and complimentary loop E. It is thus quite likely that this insertion results in significant changes to the ACh- and αBgt-binding domains. This hypothesis is supported by our observation that α7-2-nAChRs have higher affinity for ACh and bind αBgt in a rapidly reversible manner when compared to α7-1-nAChRs.

Electrophysiological studies presented herein suggest that the α7-2 splice variant may contribute to the Type II α7-nAChRs of mammalian autonomic neurons. This species of α7-nAChRs binds αBgt with high affinity and in a rapidly reversible manner. Both Type II α7-nAChRs and α7-2-nAChRs are blocked by >90% by 50 nM αBgt, and this inhibition is reversed within 5 min of toxin washout. A second distinguishing characteristic of Type II α7-nAChRs in autonomic neurons is their slow rate of desensitization. The rate of desensitization of Type I α7-nAChRs, which have been suggested to represent α7-1-nAChRs, is 10-fold faster than that of Type II α7-nAChRs (Cuevas et al., *J. Physiol.*, 2000, 525: 735-746). Data shown here indicate that α7-1-nAChRs expressed in oocytes desensitize faster than α7-2-nAChRs, further supporting the theory that the α7-2 subunit contributes to Type II α7-nAChR. Given that Type II α7-nAChRs mediate ~50% of whole-cell nicotinic responses in intracardiac and superior cervical ganglion neurons, α7-2-nAChRs may represent a significant population of AChRs in peripheral neurons. It is interesting to note that one of the few characteristics associated with α7-null mice is dysfunction of the autonomic nervous system. This dysfunction may be in part due to the loss of the α7-2-nAChR subtype in the neurons. Recent experiments have shown that the effects of nicotine on the heart are in part due to activation of α7 receptors in autonomic neurons.

The observation that the α7-2 is also found in the central nervous system suggests that this subunit may also play an important role in cells of the CNS. Preliminary studies indicate that the α7-1 and α7-2 subunits are differentially distributed in the central nervous system, and that the expression level of α7-2 is altered in the APP-PS1 transgenic mouse model of Alzheimer's disease. It is of significant interest to determine if α7-2-nAChRs also exhibit high affinity for the β-amyloid peptide, as reported for α7-1-nAChRs.

The experimental data disclosed herein show the first evidence for acetylcholine receptor diversity resulting from transcriptional modifications. The present finding of a novel α7 nicotinic receptor subunit isoform, α7-2, may in part explain the multiplicity of α7-nAChR function. The α7-2 isoform contributes to AChRs with pharmacological and biophysical properties distinct from those of α7-1-nAChRs and closely resembling those of α7-nAChRs found in intrinsic cardiac neurons and Type II α7-nAChRs of superior cervical ganglion neurons. The presence of α7-2 transcripts and protein in peripheral and central neurons suggests that this receptor subunit may contribute to cell-to-cell signaling in both branches of the nervous system.

EXAMPLE 9

Murine Homologue of the α7-2 Splice Variant

The present inventors have also identified the sequence for exon 4A of the α7-2 subunit in the mouse genome:

gtgtctgttgcatttgaccaagatcg-gcagaacatgcttctcagagaaacatatgcacaggctgaagaagatcta (SEQ ID NO:14). The sequence shows 95% homology to the nucleic acid sequence of the rat exon 4A (SEQ ID NO:5).

The mouse α7 mRNA sequence (NCBI Accession Number L37663) was compared to the corresponding human sequence (NCBI Accession Numbers AF029837, AF029838, AF029839, AF036903, and AF037646) to confirm the 3' end of exon 4 and the 5' end of exon 5. With these sequences, intron 4 of the mouse α7 gene was extracted from the mouse genomic sequence available from NCBI. The sequence of intron 4 was then compared for homology to the rat α7 exon 4a using the BLAST 2 sequences program.

EXAMPLE 10

Identification of α7-2 Splice Variant in a Transgenic Mouse Model (APP-PS1) of Alzheimer's Disease (AD)

The α7-2 splice variant has been identified in an APP-PS1 transgenic mouse model of AD. Homomeric receptors containing either the conventional (α7-1) isoform (α7-1-AChRs) or the α7-2 variant bind α-bungarotoxin (αBgt) with high affinity. However, α7-2-AChRs bind αBgt reversibly and desensitize slowly as compared to α7-1-AChRs. α7-AChRs have been shown to bind Aα1-42, a key component of the amyloid plaques associated with AD. Recent work shows age-associated changes in the levels of the α7 receptor in the hippocampus of a similar transgenic mouse model of AD.

The regional localization of both α7 isoforms with the anti-α7 mAb319 (FABGENNIX, Inc. Shreveport, La.), and that of the α7-2 subunits, was examined with immunohistochemistry using a sub-type selective polyclonal antibody. Immunoblot and quantitative PCR techniques were used to assess protein and mRNA levels as a function of age in APP-PS1 mice. α7-2 subunits are ubiquitously expressed in neurons in cortex, hippocampus, striatum, and cerebellum of all mice examined. The pyramidal layer of the hippocampus and dentate gyrus were intensely stained. This pattern was similar to that observed with mAb 319. A notable difference was seen in the staining patterns of cerebellar Purkinje cells of all mice; mAb319 intensely stained the neurons, but α7-2 antisera did not. APP-PS1 mice differ from their wild-type counterparts with significant staining of the hippocampal molecular layer with α7-2 antisera.

All patents, patent applications, provisional applications, and publications referred to or cited herein are incorporated by reference in their entirety, including all figures, tables, nucleic acid sequences, amino acid sequences, or drawings, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

---

What is claimed is:

1. An isolated polynucleotide encoding a functional α7 nicotinic acetylcholine receptor (nAChR) subunit comprising the amino acid sequence of SEQ ID NO:15, wherein said α7 nAChR subunit is capable of assembly into an ion-conducting nAChR.

2. The polynucleotide of claim 1, wherein said functional α7 nAChR subunit comprises the amino acid sequence of SEQ ID NO:1.

3. A host cell that has been genetically modified with a polynucleotide encoding a functional α7 nicotinic acetylcholine receptor (nAChR) subunit comprising the amino acid sequence of SEQ ID NO:15, wherein said α7 nAChR subunit is capable of assembly into an ion-conducting nAChR.

4. The genetically modified host cell of claim 3, wherein said functional α7 nAChR subunit comprises the amino acid sequence of SEQ ID NO:1.

5. The genetically modified host cell of claim 4, wherein said cell is selected from the group consisting of a bacterial cell, a mammalian cell, a yeast cell, an amphibian cell, and a starfish cell.

6. A nucleic acid vector comprising a polynucleotide operably linked to a promoter sequence that directs the transcription of said polynucleotide, wherein said polynucleotide encodes a functional α7 nicotinic acetylcholine receptor (nAChR) subunit comprising the amino acid sequence of SEQ ID NO:15, wherein said α7 nAChR subunit is capable of assembly into an ion-conducting nAChR.

7. The nucleic acid vector of claim 6, wherein said functional α7 nAChR subunit comprises the amino acid sequence of SEQ ID NO:1.

8. A method for producing a functional α7 nicotinic acetylcholine receptor (nAChR) subunit, comprising genetically modifying an isolated host cell to express the polynucleotide of claim 1, wherein the α7 nAChR subunit is thereby produced by the host cell.

9. The method of claim 8, wherein the cC nAChR subunit comprises the amino acid sequence of SEQ ID NO:1.

* * * * *

UNITED STATES PATENT AND TRADEMARK OFFICE
CERTIFICATE OF CORRECTION

PATENT NO. : 7,563,595 B2
APPLICATION NO. : 10/703953
DATED : July 21, 2009
INVENTOR(S) : Javier Cuevas and Emily Severance It is certified that error appears in the above-identified patent and that said Letters Patent is hereby corrected as shown below:

Column 2,
Line 27-29,

"gggtgtcagttgcattgaccaagatctgcagaacatgcttctcagagaagcatgtgcacaggctggagaagatctaagagtcagt"

should read

--gggtgtcagttgcattttgaccaagatctgcagaacatgcttctcagagaagcatgtgcacaggctggagaagatctaagagtcagt--

Column 9,
Line 42,

"8, 9, 1, 11, 12, 13, 14, 15," should read --8, 9, 10, 11, 12, 13, 14,--.

Column 16,
Line 4,

"[125I]α-bungarotoxin" should read --[125I]α-bungarotoxin--.

Column 24,
Line 1

"cc7 gene" should read --α7 gene--.

UNITED STATES PATENT AND TRADEMARK OFFICE
CERTIFICATE OF CORRECTION

PATENT NO. : 7,563,595 B2
APPLICATION NO. : 10/703953
DATED : July 21, 2009
INVENTOR(S) : Javier Cuevas and Emily Severance It is certified that error appears in the above-identified patent and that said Letters Patent is hereby corrected as shown below:

Column 26,
Last Line, Table 2

"REV  CTTGGTTCAAAATGCAACTGACACC (SEQ ID NO:9)" should read

--REV  CTTGGTCAAAATGCAACTGACACC (SEQ ID NO:9)--.

Column 48,
Line 31 (Claim 9)

"wherein the cC nAChR" should read --wherein the α7 nAChR--.

Signed and Sealed this

Twenty-second Day of September, 2009

David J. Kappos
*Director of the United States Patent and Trademark Office*